US011998620B2

(12) United States Patent
Basilion et al.

(10) Patent No.: US 11,998,620 B2
(45) Date of Patent: Jun. 4, 2024

(54) PSMA TARGETED COMPOUNDS AND USES THEREOF

(71) Applicant: CASE WESTERN RESERVE UNIVERSITY, Cleveland, OH (US)

(72) Inventors: James Basilion, Cleveland, OH (US); Zhenghong Lee, Cleveland, OH (US); Xinning Wang, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 0 days.

(21) Appl. No.: 18/456,931

(22) Filed: Aug. 28, 2023

(65) Prior Publication Data

US 2023/0414795 A1 Dec. 28, 2023

Related U.S. Application Data

(63) Continuation-in-part of application No. PCT/US2022/079566, filed on Nov. 9, 2022.

(60) Provisional application No. 63/359,257, filed on Jul. 8, 2022, provisional application No. 63/348,544, filed on Jun. 3, 2022, provisional application No. 63/277,426, filed on Nov. 9, 2021.

(51) Int. Cl.
*A61K 51/04* (2006.01)
*C07B 59/00* (2006.01)

(52) U.S. Cl.
CPC ........ *A61K 51/0485* (2013.01); *C07B 59/008* (2013.01); *A61K 2121/00* (2013.01); *C07B 2200/05* (2013.01)

(58) Field of Classification Search
CPC .............. A61K 51/0485; C07B 59/008; C07B 2200/05
USPC ........................................................ 424/1.65
See application file for complete search history.

(56) References Cited

U.S. PATENT DOCUMENTS

| 3,909,093 | A   | 9/1975  | Lundberg         |
|-----------|-----|---------|------------------|
| 6,479,470 | B1  | 11/2002 | Kozikowski et al.|
| 6,528,499 | B1  | 3/2003  | Kozikowski et al.|
| 7,038,078 | B2  | 5/2006  | Aldrich et al.   |
| 7,381,745 | B2  | 6/2008  | Kozikowski et al.|
| 7,408,079 | B2  | 8/2008  | Pomper et al.    |
| 8,078,264 | B2  | 12/2011 | Basilion         |
| 8,227,634 | B2  | 7/2012  | Pomper et al.    |
| 8,609,721 | B2  | 12/2013 | Kozikowski et al.|
| 8,778,305 | B2  | 7/2014  | Pomper et al.    |
| 8,907,058 | B2  | 12/2014 | Low et al.       |
| 9,056,841 | B2  | 6/2015  | Pomper et al.    |
| 9,192,302 | B2  | 11/2015 | Basilion         |
| 9,193,763 | B2  | 11/2015 | Low et al.       |
| 9,226,981 | B2  | 1/2016  | Pomper et al.    |
| 9,271,653 | B2  | 3/2016  | Basilion         |
| 9,314,538 | B2  | 4/2016  | Satpayev et al.  |
| 9,371,360 | B2  | 6/2016  | Pomper et al.    |
| 9,694,091 | B2  | 7/2017  | Pomper et al.    |
| 9,713,649 | B2* | 7/2017  | Huang ............... A61K 49/0032 |
| 9,776,977 | B2  | 10/2017 | Pomper et al.    |
| 9,861,713 | B2  | 1/2018  | Pomper et al.    |
| 9,884,132 | B2  | 2/2018  | Pomper et al.    |
| 9,889,199 | B2* | 2/2018  | Basilion ............ A61K 49/0052 |
| 9,925,273 | B2  | 3/2018  | Pereira et al.   |
| 9,951,324 | B2  | 4/2018  | Low et al.       |
| 10,011,657| B2  | 7/2018  | Gish et al.      |
| 10,029,023| B2  | 7/2018  | Pomper et al.    |
| 10,039,845| B2  | 8/2018  | Pomper et al.    |
| 10,046,054| B2  | 8/2018  | Low et al.       |
| RE47,103  | E   | 10/2018 | Morrison         |
| 10,188,754| B2  | 1/2019  | Yang et al.      |
| 10,207,005| B2  | 2/2019  | Basilion et al.  |
| 10,232,058| B2  | 3/2019  | Pomper et al.    |
| 10,363,313| B2  | 7/2019  | Basilion et al.  |
| 10,369,113| B2  | 8/2019  | Chandran et al.  |
| 10,406,240| B2  | 9/2019  | Low et al.       |
| 10,426,850| B2  | 10/2019 | Yu et al.        |
| 10,434,194| B2  | 10/2019 | Basilion et al.  |
| 10,485,878| B2  | 11/2019 | Low et al.       |
| 10,500,292| B2  | 12/2019 | Pomper et al.    |
| 10,517,956| B2  | 12/2019 | Low et al.       |
| 10,517,957| B2  | 12/2019 | Low et al.       |
| 10,557,128| B2  | 2/2020  | Low et al.       |
| 10,596,259| B2  | 3/2020  | Savariar et al.  |
| 10,624,969| B2  | 4/2020  | Low et al.       |
| 10,624,970| B2  | 4/2020  | Low et al.       |
| 10,624,971| B2  | 4/2020  | Low et al.       |
| 10,646,581| B2  | 5/2020  | Low et al.       |

(Continued)

FOREIGN PATENT DOCUMENTS

WO    2008/057437 A1    5/2008
WO    2010/018230 A2    2/2010

(Continued)

OTHER PUBLICATIONS

Ikeda, Masato, et al., "Supramolecular hydrogel capsule showing prostate specific antigen-responsive function for :; ensing and targeting prostate cancer cells", Chem. Sci., Jan. 2010, 491-498.
Kularatne, Sumith A., et al., "Synthesis and Biological Analysis of Prostate-Specific Membrane Antigen-Targeted Anticancer Prodrugs", Journal of Medicinal Chemistry, vol. 53, No. 21, Nov. 11, 2010, pp. 7767-7777, KP055103918.
Agnes et al., An Optical Probe for Noninvasive Molecular Imaging of Orthotopic Brain Tumors Overexpressing Epidermal Growth Factor Receptor, Mol Cancer Ther, vol. 11(10): OF1-0F10, (published on line Jul. 17, 2012).
Bennike {Development of a Novel Peptide Based Probe for Tumour Imaging, Aalborg University, Thesis {Jun. 2011 ), 92 pages.
Cheng et al. Highly Efficient Drug Delivery with Gold Nanoparticle Vectors for in Vivo Photodynamic Therapy of Cancer. J. Am. Chem. Soc. 2008, 130, 10643-10647.

(Continued)

Primary Examiner — Michael G. Hartley
Assistant Examiner — Sean R Donohue
(74) Attorney, Agent, or Firm — TAROLLI, SUNDHEIM, COVELL & TUMMINO, LLP

(57) ABSTRACT

PSMA targeted compounds, pharmaceutical compositions comprising these compounds, and methods for treating and detecting cancers in a subject are described herein.

1 Claim, 10 Drawing Sheets

(56) References Cited

U.S. PATENT DOCUMENTS

| | | | |
|---|---|---|---|
| 10,653,806 B2 | 5/2020 | Pomper et al. | |
| 10,660,971 B2 | 5/2020 | Li | |
| 10,683,272 B2 | 6/2020 | Ray et al. | |
| 10,688,198 B2 | 6/2020 | Ray et al. | |
| 10,709,794 B2 | 7/2020 | Basilion et al. | |
| 10,717,750 B2 | 7/2020 | Pomper et al. | |
| 10,722,593 B2 | 7/2020 | Vining et al. | |
| 10,736,974 B2 | 8/2020 | Pomper et al. | |
| 10,744,206 B2 | 8/2020 | Li | |
| 10,918,741 B2 * | 2/2021 | Huang | A61K 49/0032 |
| 11,202,836 B2 | 12/2021 | Basilion et al. | |
| 2006/0222595 A1 | 10/2006 | Mukherjee et al. | |
| 2007/0160617 A1 | 7/2007 | Ma et al. | |
| 2008/0193381 A1 | 8/2008 | Babich et al. | |
| 2008/0213377 A1 | 9/2008 | Bhatia et al. | |
| 2009/0011004 A1 | 1/2009 | Lutz et al. | |
| 2009/0061010 A1 | 3/2009 | Zale et al. | |
| 2009/0297615 A1 | 12/2009 | Wang et al. | |
| 2009/0304803 A1 | 12/2009 | Hasan | |
| 2010/0026068 A1 | 2/2010 | Yoo et al. | |
| 2010/0183504 A1 | 7/2010 | Chen | |
| 2010/0329983 A1 | 12/2010 | Stewart | |
| 2011/0165079 A1 | 7/2011 | Lu et al. | |
| 2011/0262347 A1 | 10/2011 | Ruoslahti et al. | |
| 2011/0268660 A1 | 11/2011 | Danikas et al. | |
| 2012/0282632 A1 | 11/2012 | Chiu et al. | |
| 2012/0323164 A1 | 12/2012 | Kenney et al. | |
| 2013/0034494 A1 * | 2/2013 | Babich | C07D 257/02 534/10 |
| 2013/0289520 A1 | 10/2013 | Febvay et al. | |
| 2013/0315834 A1 | 11/2013 | Praveen et al. | |
| 2014/0220143 A1 | 8/2014 | Dhar et al. | |
| 2014/0286969 A1 | 9/2014 | Tschoepe et al. | |
| 2015/0056132 A1 | 2/2015 | Dennis et al. | |
| 2015/0366968 A1 * | 12/2015 | Basilion | A61K 47/64 604/20 |
| 2016/0067341 A1 | 3/2016 | Low et al. | |
| 2018/0106809 A1 | 4/2018 | Dennis et al. | |
| 2019/0010237 A1 | 1/2019 | Reilly et al. | |
| 2019/0099431 A1 | 4/2019 | Gish et al. | |
| 2019/0111150 A1 | 4/2019 | Singh et al. | |
| 2019/0262417 A1 | 8/2019 | Leanna et al. | |
| 2019/0328898 A1 | 10/2019 | Torgov et al. | |
| 2019/0328911 A1 | 10/2019 | Krol et al. | |
| 2020/0199245 A1 | 6/2020 | Liu et al. | |
| 2020/0215200 A1 | 7/2020 | Allan et al. | |
| 2020/0276331 A1 | 9/2020 | Coumans | |
| 2020/0282072 A1 | 9/2020 | Tschoepe et al. | |
| 2023/0046947 A1 | 2/2023 | Nyanguile et al. | |

FOREIGN PATENT DOCUMENTS

| | | |
|---|---|---|
| WO | 2011/106639 A1 | 9/2011 |
| WO | 2012/106713 A2 | 8/2012 |
| WO | 2014127365 A1 | 8/2014 |

OTHER PUBLICATIONS

Choi et al. Mechanism of active targeting in solid tumors with transferrin-containing gold nanoparticles. Proc Natl Acad Sci USA. Jan. 19, 2010;107(3):1235-1240.

Craig et al., Langmuir, vol. 24:10282-10292 (2008) {Year: 2008).

DeJesus, Synthesis of [64Cu]Cu-NOTA-Bn—GE11 for PET Imaging of EGFR-Rich Tumors, Current Radiopharmaceuticals, vol. 5(1):15-18 {Jan. 2012).

Ikuta et al. The effect of molecular structure on the anticancer drug release rate from prodrug nanoparticles. 2015,51, 12835-12838.

Li et al. Identification and characterization of a novel peptide ligand of epidermal growth factor receptor for targeted delivery of therapeutics. The FASEB J. 2005 19(14):1978-1984.

Liu et al. {Spacer length effects on in vitro imaging and surface accessibility of fluorescent inhibitors of prostate specific membrane antigen, Bioorganic & Medicinal Letters, vol. 21 :7013-7016.

Otsuka et al. PEGylated nanoparticles for biological and pharmaceutical applications. vol. 55, Issue 3, Feb. 24, 2003, pp. 403-419.

Samia et al. Semiconductor Quantum Dots for Photodynamic Therapy. J. Am. Chem. Soc. 2003, 125:15736.

Song et al. (Peptide Ligand-mediated liposome distribution and targeting to EGFR expressing tumor in vivo, International Journal of Pharmaceutics, vol. 363:155-161 (pub online Jul. 23, 2008).

Steichen et al. A review of current nanoparticle and targeting moieties for the delivery of cancer therapeutics. Feb. 14, 2013; 48(3): 416-427.

Vagner et al., Bioorganic & Medicinal Chemistry Letter, vol. 14:211-215 (2004).

Huang, Steve S., "Improving the Distribution of PSMA-Targeting Tracers With a Highly Negatively Charged Linker" The Prostate 74:702-713 (2014).

Kassis, Amin I., "Therapeutic Radionuclides: Biophysical and Radiobiologic Principles" Semin Nucl Med. Sep. 2008; 38(5) 358-366.

Lauri, Chiara, et al. "PSMA Expression in Solid Tumors beyond the Prostate gland: Ready for Theranostic Applications" J. Clin. Med. Nov. 2022, p. 1-20.

Laydner, Humberto, et al., "Robotic Real-Time Near Infrared Targeted Fluorescence Imaging in a Murine Model of Prostate Cancer: A Feasibility Study", Urology 81 (2), 2013.

Wang, Xinning, et al., "Development of Targeted Near-Infrared Imaging Agents for Prostate Cancer", Mol Cancer Ther, 13(11) Nov. 2014.

Thiele, Nikki A., et al., "Actinium-225 and Targeted alpha therapy: Coordination Chemistry and Current Chelation Approaches", Cancer Biotherapy and Radiopharmaceuticals, vol. 33, No. 8, 2018.

* cited by examiner

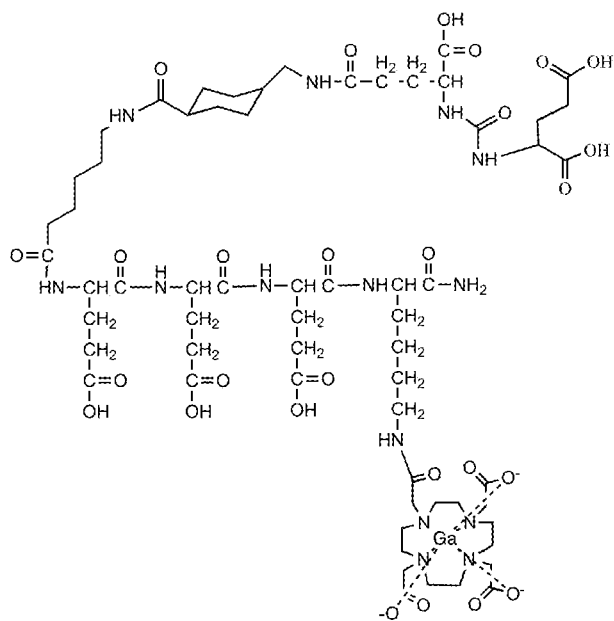
PSMA-1-DOTA
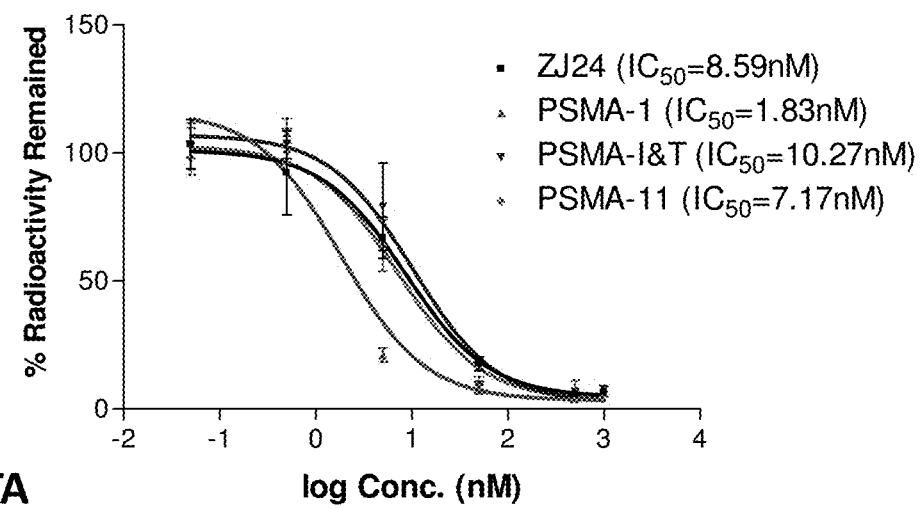
Data Table-1
- ZJ24 ($IC_{50}$=8.59nM)
- PSMA-1 ($IC_{50}$=1.83nM)
- PSMA-I&T ($IC_{50}$=10.27nM)
- PSMA-11 ($IC_{50}$=7.17nM)
PSMA-1-DOTA
- 4-6 fold higher affinity than other PSMA-targeting ligands
- Utilizes D-amino acids for stability
- IC50 for PSMA-617 = 3.3 nM (Wurzer et al., JNM, 2022)
Fig. 3

[$^{68}$Ga]PSMA-1-DOTA/PSMA-11 Comparison PET Scan

[$^{68}$Ga]PSMA-1-DOTA does not bind to salivary glands, little kidney uptake

[$^{68}$Ga]PSMA-11 has significant salivary and kidney uptake

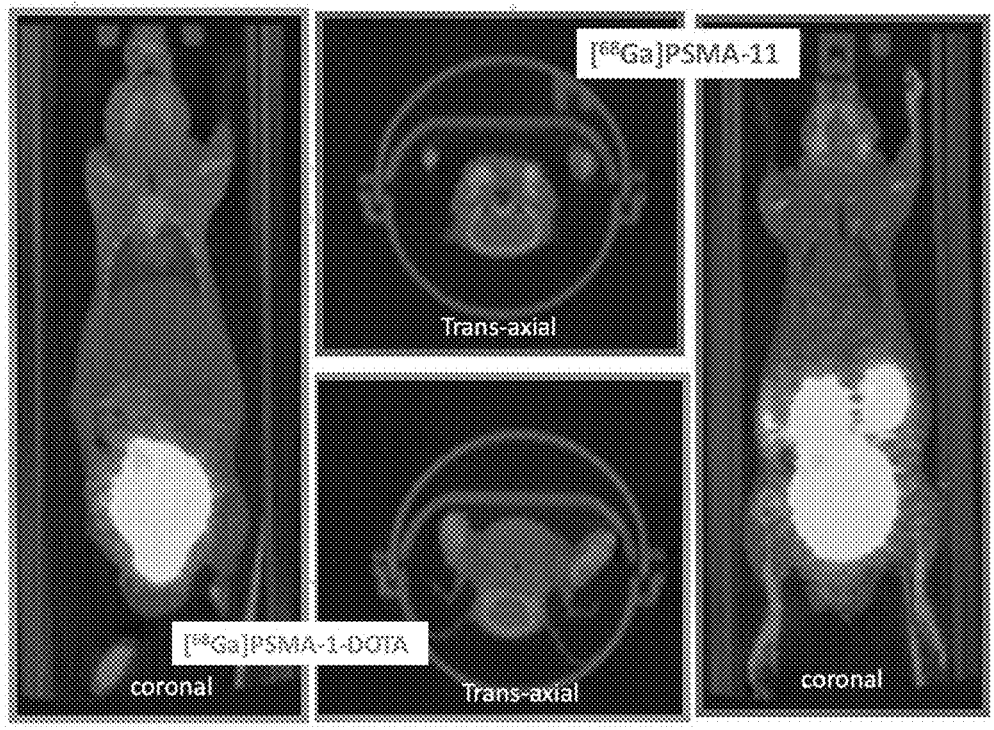

[$^{68}$Ga] PSMA-1-DOTA/PSMA-11 comparison
- Animals without tumor
- Comparison performed in same animal separated by 24 hours
- [$^{68}$Ga]PSMA-1-DOTA was administered first
- Data is normalized and on same scale
- Doses similar and ranging from 3.7-7.5 MBq (100 – 200 uCi)

Fig. 5

[⁶⁸Ga]PSMA-1-DOTA/PSMA-11 comparison PET-scan in tumor bearing animals (maximum intensity projection, MIP)

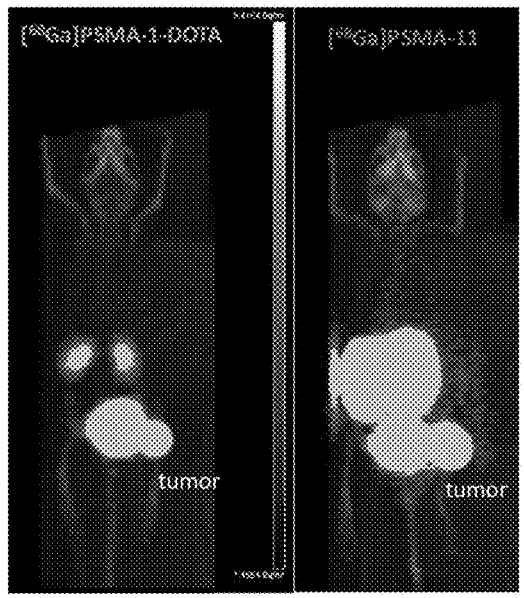

[⁶⁸Ga]PSMA-1-DOTA
- Significant uptake in tumor
- Relatively little uptake in kidney
- No detectable uptake in salivary gland
- Renally cleared

[⁶⁸Ga]PSMA-11
- High uptake in kidney
- High uptake in salivary and lacrimal glands
- Significant uptake in tumor
- Renally cleared

[⁶⁸Ga]PSMA-1-DOTA/PSMA-11 comparison
- Animals bearing PC3pip tumors
- Comparison performed in same animal separated by 24 hours
- PSMA-1-DOTA was administered first
- Study using the same dose and same scale
- Doses similar and ranging from 3.7-7.5 MBq (100 – 200 uCi)

Fig. 6

Mean SUV for PSMA-1, PSMA I&T, PSMA-11

PSMA TARGETED COMPOUNDS AND USES THEREOF

RELATED APPLICATION

This application is a Continuation-in-Part of PCT/US2022/079566, filed Nov. 9, 2022, which claims priority to U.S. Provisional Application Nos. 63/348,544, filed Jun. 3, 2022, and 63/277,426, filed Nov. 9, 2021, and 63/359,257, filed Jul. 8, 2022, the subject matter of which are incorporated herein by reference in their entirety.

TECHNICAL FIELD

This application relates to prostate-specific membrane antigen (PSMA) targeted compounds and to their use in compositions for targeting, imaging, and treating cancer.

BACKGROUND

Radionuclides have potential utility in cancer diagnosis and therapy, particularly if they can be delivered selectively to a target location within the body of a subject. Targeted delivery of radionuclides can be achieved by using constructs that are engineered to both securely retain the radionuclide for in vivo delivery and deliver the radionuclide selectively to a desired location within the body, with a reasonably low level of delivery to non-target regions of the body. Targeting constructs have been developed that target a desired region of the body covalently coupled to a chelator via a suitable linker to secure radionuclides for such purposes.

An example of a cancer target is prostate-specific membrane antigen (PSMA). PSMA is a 120 kDa protein expressed in prostate tissues and was originally identified by reactivity with a monoclonal antibody designated 7E11-05 (Horoszewicz et al., 1987, Anticancer Res. 7:927-935; U.S. Pat. No. 5,162,504). PSMA is characterized as a type II transmembrane protein sharing sequence identity with the transferrin receptor (Israeli et al., 1994, Cancer Res. 54:1807-1811). PSMA is a glutamate carboxy-peptidase that cleaves terminal carboxy glutamates from both the neuronal dipeptide N-acetylaspartylglutamate (NAAG) and gamma-linked folate polyglutamate. That is, expression of PSMA cDNA confers the activity of N-acetylated α-linked acidic dipeptidase or "NAALADase" activity (Carter et al., 1996, PNAS 93:749-753).

PSMA is expressed in increased amounts in prostate cancer. As a prostate carcinoma marker, PSMA is believed to serve as a target for imaging and cytotoxic treatment modalities for prostate cancer. Prostate carcinogenesis, for example, is associated with an elevation in PSMA abundance and enzymatic activity of PSMA. PSMA antibodies, particularly indium-111 labeled and tritium labeled PSMA antibodies, have been described and examined clinically for the diagnosis and treatment of prostate cancer. PSMA is expressed in prostatic ductal epithelium and is present in seminal plasma, prostatic fluid and urine.

Recent evidence suggests that PSMA is also expressed in tumor associated neovasculature of a wide spectrum of malignant neoplasms including conventional (clear cell) renal carcinoma, transitional cell carcinoma of the urinary bladder, testicular embryonal carcinoma, colonic adenocarcinoma, neuroendocrine carcinoma, glioblastoma multiforme, malignant melanoma, pancreatic ductal carcinoma, non-small cell lung carcinoma, soft tissue carcinoma, breast carcinoma, and prostatic adenocarcinoma. (Chang et al. (1999) Cancer Res. 59, 3192-3198).

In addition to prostate cancer and other proliferating or neoplastic cells, normal tissues can also express PSMA or PSMA-like molecules with the highest density of non-cancer tissue expression in the kidneys, lacrimal glands, and salivary glands.

SUMMARY

Embodiments described herein relate to PSMA targeted compounds, pharmaceutical compositions comprising these compounds, and methods for treating and detecting cancers (e.g., prostate cancer) in a subject in need thereof. The PSMA targeted compounds include a PSMA ligand, e.g., PSMA-1, coupled to a metal chelating agent or chelated metal nuclide. Advantageously, the PSMA targeted compounds have similar standard uptake values (SUVs) in salivary glands, lacrimal glands, and non-PSMA expressing muscle tissue, and substantially lower SUVs in salivary glands, lacrimal glands, and non-PSMA expressing muscle tissue as compared to SUVs in PSMA-expressing cancer tissue upon administration to a subject as can be measured by positron emission tomography (PET).

In some embodiments, the PSMA targeted compound can have formula (IA):

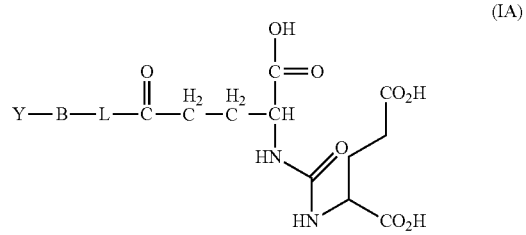

(IA)

or a pharmaceutically acceptable salt thereof,
wherein:
L is a linker from 3 to 11 atoms in length comprising optionally substituted linear alkylene and a heterocyclic or cycloalkylene ring;
B is a 2 to 5 amino acid peptide linker;
Y includes at least one of a metal chelating agent or a chelated metal nuclide; and
wherein the compound has similar uptake in salivary glands and non-PSMA expressing muscle tissue and wherein said uptake is substantially lower than in PSMA-expressing cancer tissue upon administration to a subject.

In other embodiments, the PSMA targeted compound can have formula (IB):

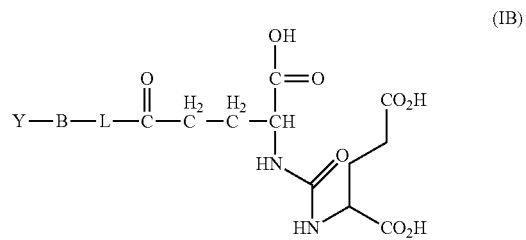

(IB)

or a pharmaceutically acceptable salt thereof, wherein:

L is a linker from 3 to 11 atoms in length comprising optionally substituted linear alkylene and a heterocyclic or cycloalkylene ring;

B is a 2 to 5 amino acid peptide linker;

Y includes at least one of a metal chelating agent or a chelated metal nuclide; and wherein the compound in the absence of Y has a net negative charge under standard physiological conditions; and wherein the compound has a calculated log P (C log P) less than −10 when devoid of the metal nuclide.

In still other embodiments, the PSMA targeted compound can have formula (IC):

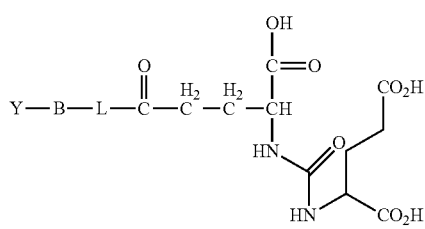
(IB)

or a pharmaceutically acceptable salt thereof, wherein:

L includes a C3-C7 linear alkylene and/or a ring selected from an optionally substituted 4 to 7 membered non-aromatic heterocyclic ring or an optionally substituted C4-C7 cycloalkylene ring;

B is a 2 to 5 amino acid peptide linker consisting of up to 4 amino acids selected from aspartic acid or glutamic acid and optionally one other amino acid;

Y includes at least one of a metal chelating agent or a chelated metal nuclide; and wherein the compound has similar uptake in salivary glands and non-PSMA expressing muscle tissue and wherein said uptake is substantially lower than in PSMA-expressing cancer tissue upon administration to a subject.

In some embodiments, the compound in the absence of Y has a net negative charge under standard physiological conditions.

In other embodiments, the compound can have a calculated log P (clog P) less than −10 when devoid of the metal nuclide.

In some embodiments, B has the following formula:

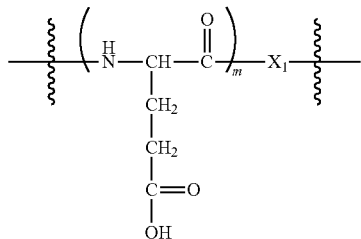

wherein m is 1, 2, 3, or 4 and $X_1$ is an amino acid.

In other embodiments, B has the following formula:

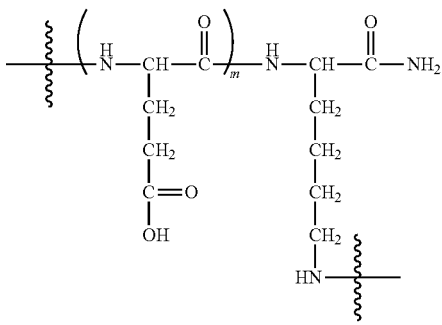

wherein m is 1, 2, 3, or 4.

In some embodiments, the compound has the general formula:

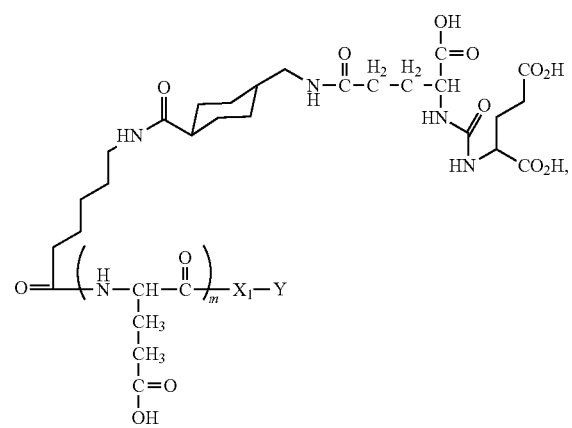

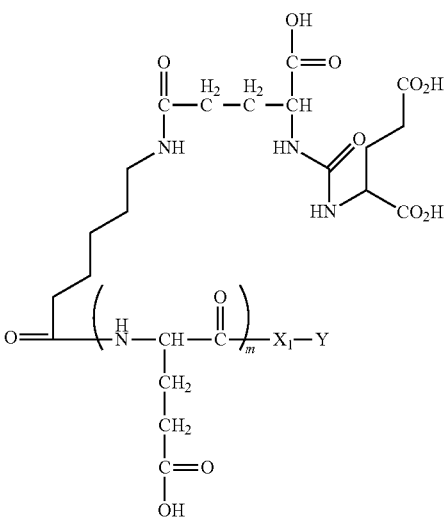

or a pharmaceutically acceptable salt thereof; wherein m is 1, 2, 3, or 4;

$X_1$ is an amino acid; and

Y includes at least one of a metal chelating agent or a chelated metal nuclide.

In some embodiments, compound has the general formula:

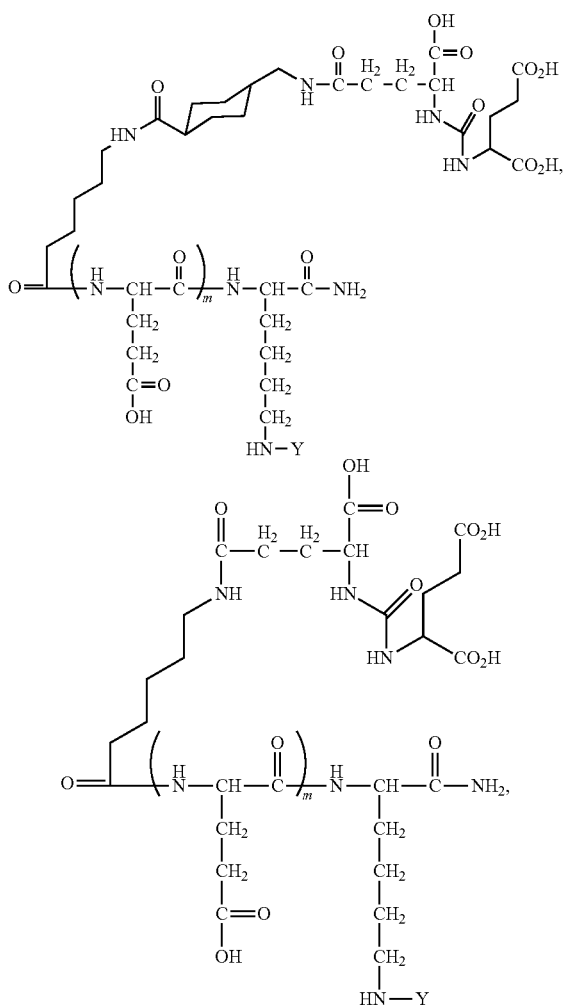

or a pharmaceutically acceptable salt thereof;
wherein
m is 1, 2, 3, or 4; and
Y includes at least one of a metal chelating agent or chelated metal nuclide.

In some embodiments, the chelating agent includes at least one of diethylenetriaminepentaacetate (DTPA), 1,4,7,10-tetraazadodecanetetraacetate (DOTA), 2,2',2''-(10-(pyridin-2-ylmethyl)-1,4,7,10-tetraazacyclododecane-1,4,7-triyl) triacetic acid (DOTA-1Py), 2,2'-(7,10-(pyridin-2-ylmethyl)-1,4,7,10-tetraazacyclododecane-1,4-diyl) diacetic acid (DOTA-2Py), 2-(4,7,10-tris (pyridin-2-ylmethyl)-1,4,7,10-tetraazacyclododecane-1-yl) acetic acid (DOTA-3Py), 1,4,7,10-tetraazadodecane-1,4,7-triacetate (DO3A), ethylenediaminetetraacetate (EDTA), 1,4,7,10-tetraazacyclotridecanetetraacetic acid (TRITA), 1,4,8,11-tetraazacyclotetradecane-1,4,8,11-tetraacetic acid (TETA), 1,4,7,10-tetraazadodecanetetramethylacetate (DOTMA), 1,4,7,10-tetraazadodecane-1,4,7-trimethylacetate (DO3MA), N,N',N'',N'''-tetraphosphonatomethyl-1,4,7,10-tetraazacyclododecane (DOTP), 1,4,7,10-tetraazacyclododecane-1,4,7,10-tetrakis(methylene methylphosphonic acid) (DOTMP), 1,4,7,10-tetraazacyclododecane-1,4,7,10-tetrakis(methylene phenylphosphonic acid) (DOTPP), N,N'-ethylenedi-L-cysteine, 1,4,7-triazacyclononane (TACN), N,N'-Bis(2-hydroxy-5-(ethylene-beta-carboxy)benzyl) ethylenediamine N,N'-diacetic acid (HBED-CC), S-2-(4-isothiocyanatobenzyl)-1,4,7,10-tetraazacylododecane tetracetic acid (p-SCN-Bn-DOTA), 2-(4-isothiocyanatobenzyl-1,4,7,10-tetraaza-1,4,7,10,tetra-(2-carbamonylmethyl)-cyclododecane (p-SCN-Bn-TCMC), MeO-DOTA-NCS, [(R)-2-Amino-3-(4-isothiocyanatophenyl)propyl]-trans-(S, S)-cyclohexane-1,2-diamine-pentaacetic acid (CHX-A''-DTPA-NCS), 2-[4-nitrobenzyl]-1,4,7,10,13-pentaazacyclopentadecane-N,N',N'',N''',N''''-pentaacetic acid (PEPA), 1,4,7,10,13,16-hexaazacyclooctadecane-N,N',N'',N''',N''''-hexaacetic acid (HEHA), desferrioxamine B (DFO), macropa, macropa-NCS, macropid, bispa$^2$, EuK-106, 7-[2-(bis-carboxymethyl-amino)-ethyl]-4,10-bis-carboxymethyl-1,4,7,10-tetraaza-cyclododec-1-yl-acetic acid (DEPA), 3p-C-DEPA, or derivatives thereof.

In some embodiments, the metal chelating agent or chelated metal is linked directly to an amino acid residue of B with an amide bond.

In some embodiments, the chelated metal nuclide includes at least one of Ga, I, In, Y, Lu, Bi, Ac, Re, In, Th, Tc, Tl, Tb, Zr, Cu, Rb, At, Pb, Gd, Sm, or Sr.

In some embodiments, the metal chelating agent is configured or selected to chelate a therapeutic radionuclide. The therapeutic radionuclide can be selected from $^{225}$AC, $^{226}$AC, $^{227}$Th, $^{211}$Bi, $^{212}$Bi, $^{213}$Bi, $^{203}$Pb, $^{212}$Pb, or $^{177}$Lu.

In some embodiments, the compound can have the formula of:

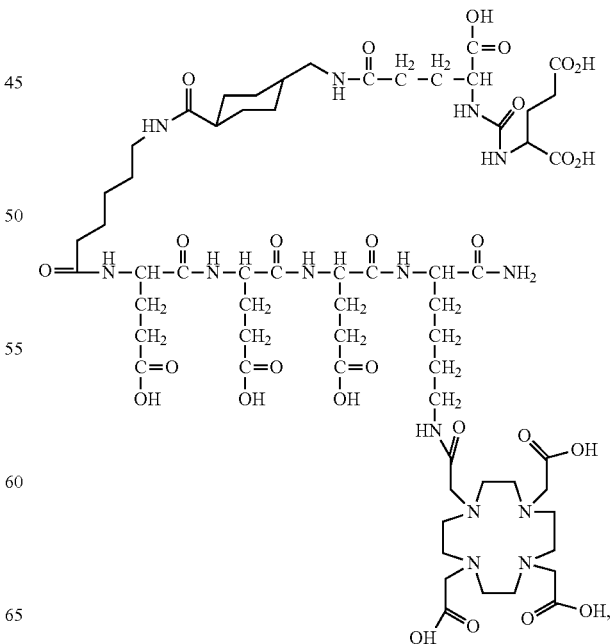

-continued

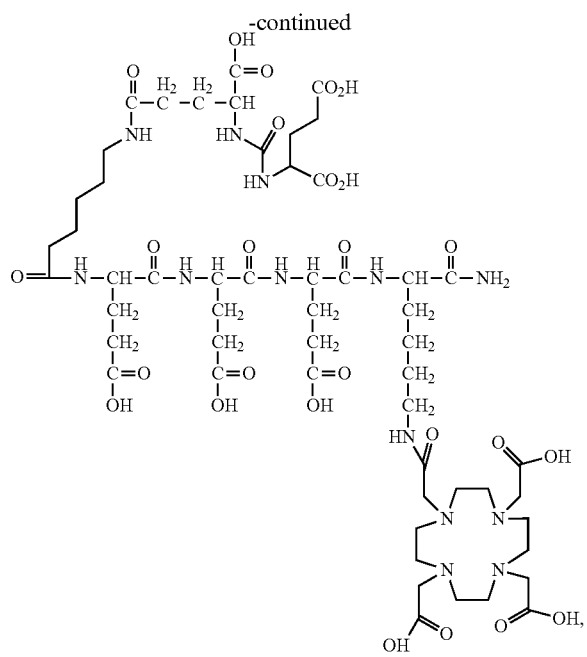

or a pharmaceutically acceptable salt thereof, optionally complexed with a metal nuclide of at least one of Ga, I, In, Y, Lu, Bi, Ac, Re, In, Th, Tc, Tl, Tb, Zr, Cu, Rb, At, Pb, Gd, Sm, or Sr.

In some embodiments, the metal nuclide can be selected from $^{225}$Ac, $^{226}$Ac, $^{227}$Th, $^{211}$Bi, $^{212}$Bi, $^{213}$Bi, $^{203}$Pb, $^{212}$Pb, or $^{177}$Lu.

Other embodiments described herein relate to a compound that has formula (II):

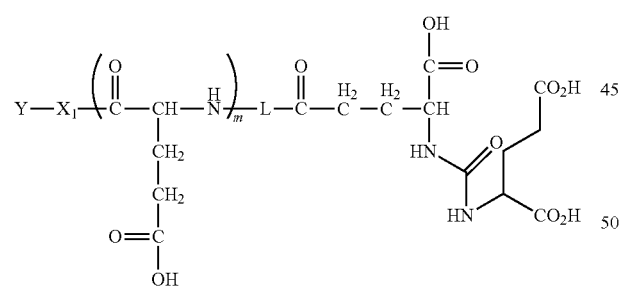

(II)

or a pharmaceutically acceptable salt thereof, wherein:
L includes a C3-C7 linear alkylene and/or a ring selected from an optionally substituted 4 to 7 membered non-aromatic heterocyclic ring or an optionally substituted C4-C7 cycloalkylene ring;
m is 1, 2, 3, or 4;
$X_1$ is an amino acid; and
Y includes at least one of a metal chelating agent or a chelated metal nuclide selected from $^{225}$Ac, $^{226}$Ac, $^{227}$Th, $^{211}$Bi, $^{212}$Bi, $^{213}$Bi, $^{203}$Pb, $^{212}$Pb, or $^{177}$Lu;

wherein the compound has similar uptake in salivary glands and non-PSMA expressing muscle tissue and wherein said uptake is substantially lower than in PSMA-expressing cancer tissue upon administration to a subject; and wherein the compound in the absence of Y has a net negative charge under standard physiological conditions.

In some embodiments, the compound can have a calculated log P (Clog P) less than −10 when devoid of the metal nuclide.

In some embodiments, the compounds can have the formula:

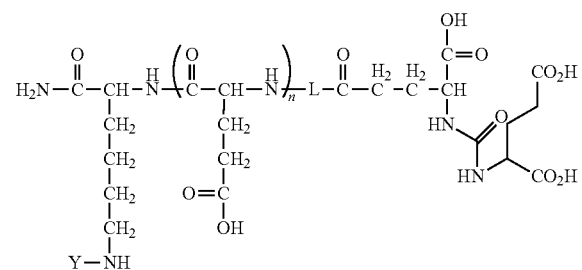

a pharmaceutically acceptable salt thereof;
wherein
L includes a C3-C7 linear alkylene and/or a ring selected from an optionally substituted 4 to 7 membered non-aromatic heterocyclic ring or an optionally substituted C4-C7 cycloalkylene ring;
m is 1, 2, 3, or 4; and
Y includes at least one metal chelating agent and chelated metal nuclide selected from $^{225}$Ac, $^{226}$Ac, $^{227}$Th, $^{211}$Bi, $^{212}$Bi, $^{213}$Bi, $^{203}$Pb, $^{212}$Pb, or $^{177}$Lu.

In some embodiments, the compound can have the formula:

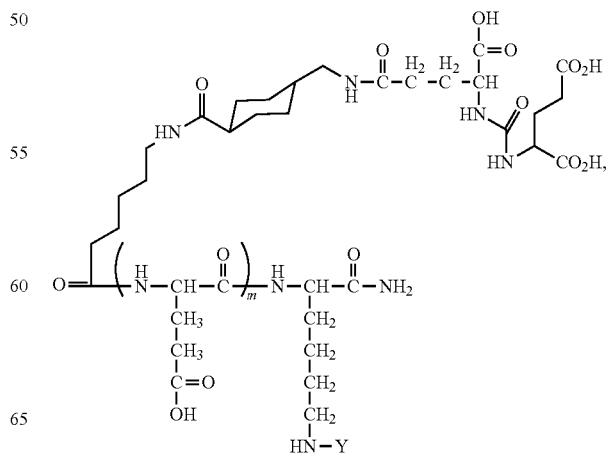

-continued

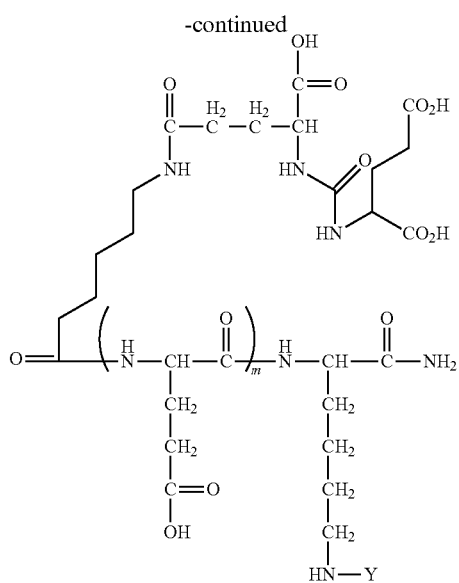

or a pharmaceutically acceptable salt thereof;
wherein
m is 1, 2, 3, or 4; and
Y includes at least one of a metal chelating agent or a chelated metal nuclide selected from $^{225}$Ac, $^{226}$AC, $^{227}$Th, $^{211}$Bi, $^{212}$Bi, $^{213}$Bi, $^{203}$Pb, $^{212}$Pb, or $^{177}$Lu.

In some embodiments, the metal chelating agent is selected from 1,4,7,10-tetraazadodecanetetraacetate (DOTA), 2,2',2"-(10-(pyridin-2-ylmethyl)-1,4,7,10-tetraazacyclododecane-1,4,7-triyl) triacetic acid (DOTA-1Py), 2,2'-(7,10-(pyridin-2-ylmethyl)-1,4,7,10-tetraazacyclododecane-1,4-diyl) diacetic acid (DOTA-2Py), 2-(4,7,10-tris (pyridin-2-ylmethyl)-1,4,7,10-tetraazacyclododecane-1-yl) acetic acid (DOTA-3Py), 1,4,7,10-tetraazadodecane-1,4,7-triacetate (DO3A), ethylenediaminetetraacetate (EDTA), 1,4,7,10-tetraazacyclotridecanetetraacetic acid (TRITA), 1,4,8,11-tetraazacyclotetradecane-1,4,8,11-tetraacetic acid (TETA), 1,4,7,10-tetraazadodecanetetramethylacetate (DOTMA), 1,4,7,10-tetraazadodecane-1,4,7-trimethylacetate (DO3MA), N,N',N",N"'-tetraphosphonatomethyl-1,4,7,10-tetraazacyclododecane (DOTP), 1,4,7,10-tetraazacyclododecane-1,4,7,10-tetrakis(methylene methylphosphonic acid) (DOTMP), 1,4,7,10-tetraazacyclododecane-1,4,7,10-tetrakis(methylene phenylphosphonic acid) (DOTPP), N,N'-ethylenedi-L-cysteine, S-2-(4-isothiocyanatobenzyl)-1,4,7,10-tetraazacyclododecane tetracetic acid (p-SCN-Bn-DOTA), 2-(4-isothiocyanatobenzyl-1,4,7,10-tetraaza-1,4,7,10,tetra-(2-carbamonylmethyl)-cyclododecane (p-SCN-Bn-TCMC), MeO-DOTA-NCS, RR)-2-Amino-3-(4-isothiocyanatophenyl)propyll-trans-(S,S)-cyclohexane-1,2-diamine-pentaacetic acid (CHX-A"-DTPA-NCS), 2-[4-nitrobenzyl]-1,4,7,10,13-pentaazacyclopentadecane-N,N',N",N"',N""-pentaacetic acid (PEPA), 1,4,7,10,13,16-hexaazacyclooctadecane-N,N',N",N"',N""-hexaacetic acid (HEHA), desferrioxamine B (DFO), macropa, macropa-NCS, macropid, bispa $^2$, EuK-106, 7-[2-(bis-carboxymethyl-amino)-ethyl]-4,10-bis-carboxymethyl-1,4,7,10-tetraaza-cyclododec-1-yl-acetic acid (DEPA), 3p-C-DEPA, or derivatives thereof.

BRIEF DESCRIPTION OF THE DRAWINGS

The following is a brief description of the drawings which are presented for the purpose of illustrating the invention and not for the purpose of limiting them.

FIG. 3 illustrates a graph comparing binding to PC3pip cells of PSMA-1-DOTA, ZJ24, PSMA-I&T, and PSMA-11.

FIG. 5 illustrates images of PET scans of healthy mice without tumors administered [$^{68}$Ga]PSMA-1-DOTA or [$^{68}$Ga]PSMA-11.

FIG. 6 illustrates images of PET scans of tumor bearing mice administered [$^{68}$Ga]PSMA-1-DOTA or [$^{68}$Ga]PSMA-11.

DETAILED DESCRIPTION

Figure 1:
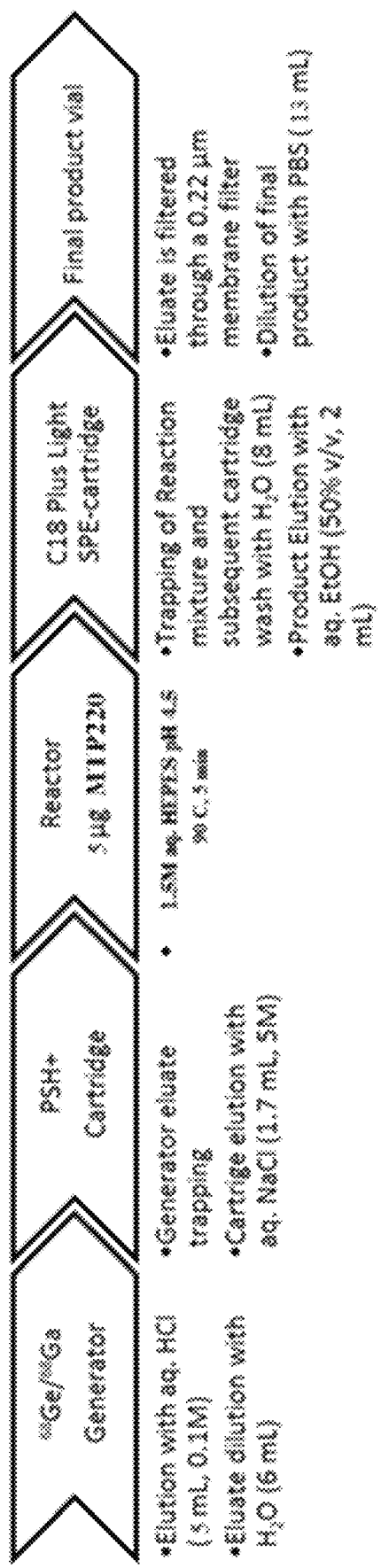
FIG. 1 is a schematic flow chart of the process for adiosynthesis of [$^{68}$Ga]PSMA-1.

All scientific and technical terms used in this application have meanings commonly used in the art unless otherwise specified. The definitions provided herein are to facilitate understanding of certain terms used frequently herein and are not meant to limit the scope of the application.

The articles "a" and "an" are used herein to refer to one or to more than one (i.e., to at least one) of the grammatical object of the article. By way of example, "an element" means one element or more than one element.

The term "calculated log P" or "C log P" refers to the log(base 10) of the n-octanol/water partition coefficient (log $P_{ow}$) as calculated using ChemDraw Professional 22.0.

The terms "comprise," "comprising," "include," "including," "have," and "having" are used in the inclusive, open sense, meaning that additional elements may be included. The terms "such as", "e.g.," as used herein are non-limiting and are for illustrative purposes only. "Including" and "including but not limited to" are used interchangeably.

The term "or" as used herein should be understood to mean "and/or" unless the context clearly indicates otherwise.

The term "agent" is used herein to denote a chemical compound, a mixture of chemical compounds, a biological macromolecule, or an extract made from biological materials.

The term "sample" can refer to a specimen or culture obtained from any source, as well as clinical, research, biological and environmental samples. Biological samples may be obtained from animals (including humans) and encompass blood, serum, urine, saliva, stool, biopsy, cells, fluids, solids, tissues, and organs, and whole organisms.

The terms "patient", "subject", "mammalian host," and the like are used interchangeably herein, and refer to humans and non-human animals (e.g., rodents, arthropods, insects, fish (e.g., zebrafish)), non-human primates, ovines, bovines, ruminants, lagomorphs, porcines, caprines, equines, or canines felines, ayes, etc.).

The terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys, and liver.

Terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, glioblastoma multiform, meningoma, medulloblastoma, schwannoma and epidymoma.

The term "chelating agent" refers to a molecule containing two or more electron donor atoms that can form coordinate bonds to a single central metal ion, e.g., to a radionuclide. Typically, chelating agents coordinate metal ions through oxygen or nitrogen donor atoms, or both. After the first coordinate bond is formed, each successive donor atom that binds creates a ring or cage containing the metal ion. A chelating agent may be bidentate, tridentate,tetradentate, etc., depending on whether it contains 2, 3, 4, or more donor atoms capable of binding to the metal ion. However, the chelating mechanism is not fully understood and depends on the chelating agent and/or radionuclide. For example, it is believed that DOTA can coordinate a radionuclide via carboxylate and amino groups (donor groups) thus forming complexes having high stability (Dai et al. *Nature Corn.* 2018, 9, 857). The expression "chelating agent" is to be understood as including the chelating agent as well as salts thereof. Chelating agents having carboxylic acid groups, e.g., DOTA, TRITA, HETA, HEXA, EDTA, DTPA etc., may, for example, be derivatized to convert one or more carboxylic acid groups to amide groups for attachment to the compound, i.e., to the reactive moiety or the linker, alternatively, for example, said compounds may be derivatized to enable attachment to the compound via one of the $CH_2$ groups in the chelate ring.

The term "polypeptide" refers to a polymer composed of amino acid residues or related naturally occurring structural variants, and synthetic non-naturally occurring analogs thereof linked via peptide bonds or modified peptide bonds (i.e., peptide isosteres), related naturally occurring structural variants, and synthetic non-naturally occurring analogs thereof, glycosylated polypeptides, and all "mimetic" and "peptidomimetic" polypeptide forms. Synthetic polypeptides can be synthesized, for example, using an automated polypeptide synthesizer. The term can refer to an oligopeptide, peptide, polypeptide, or protein sequence, or to a fragment, portion, or subunit of any of these. The term "protein" typically refers to large polypeptides. The term "peptide" typically refers to short polypeptides.

A "portion" of a polypeptide or protein means at least about three sequential amino acid residues of the polypeptide. It is understood that a portion of a polypeptide may include every amino acid residue of the polypeptide.

The term "radionuclide" as used herein refers to an atom with an unstable nucleus, which is a nucleus characterized by excess energy available to be imparted either to a newly created radiation particle within the nucleus or to an atomic electron. Radionuclides occur naturally or can be artificially produced.

The term "derivative" refers to an amino acid residue chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-benzylhistidine. Also included as derivatives are those amino acid residues, which contain one or more naturally occurring amino acid derivatives of the twenty standard amino acids, such as non-standard amino acids.

"PSMA" refers to Prostate Specific Membrane Antigen, a potential carcinoma marker that has been hypothesized to serve as a target for imaging and cytotoxic treatment modalities for cancer.

The term "standard physiological conditions" refers to a solution of pH 7.4, 150 mM ionic strength, 37° C. and 1 atmosphere pressure such as phosphate buffered saline (PBS) at 37° C.

The term "standardized uptake value (SUV)" refers to a measure of radioactivity in a specific area of interest relative to an idealized even distribution of radioactive material throughout the body. SUV is used historically by nuclear medicine professionals to distinguish between "normal" and "abnormal" levels of uptake. Preferably, uptake is measured by positron emission tomography (PET) imaging or other imaging modalities.

The terms "treating" or "treatment" of a disease can refer to executing a treatment protocol to eradicate at least one diseased cell. Thus, "treating" or "treatment" does not require complete eradication of diseased cells.

An "effective amount" can refer to that amount of a therapeutic agent that results in amelioration of symptoms or a prolongation of survival in the subject and relieves, to some extent, one or more symptoms of the disease or returns to normal (either partially or completely) one or more physiological or biochemical parameters associated with or causative of the disease.

Therapeutic agents can include any agent (e.g., molecule, drug, pharmaceutical composition, etc.) capable of preventing, inhibiting, or arresting the symptoms and/or progression of a disease.

Embodiments described herein relate to PSMA targeted compounds, pharmaceutical compositions comprising these compounds, and methods for treating and detecting cancers (e.g., prostate cancer) in a subject in need thereof. Pathological studies indicate that PSMA is expressed by virtually all prostate cancers, and its expression is further increased in poorly differentiated, metastatic, and hormone-refractory carcinomas. Higher PSMA expression is also found in cancer cells from castration-resistant prostate cancer patients. Increased PSMA expression is reported to correlate with the risk of early prostate cancer recurrence after radical prostatectomy. In addition to being overexpressed in prostate cancer (PCa), PSMA is also expressed in the neovasculature of neoplasms including but not limited to conventional (clear cell) renal carcinoma, transitional cell carcinoma of the urinary bladder, testicular embryonal carcinoma, colonic adenocarcinoma, neuroendocrine carcinoma, gliobastoma multiforme, malignant melanoma, pancreatic ductal carcinoma, non-small cell lung carcinoma, soft tissue carcinoma, breast carcinoma, and prostatic adenocarcinoma.

The PSMA targeted compounds described herein include a PSMA ligand, e.g., PSMA-1, conjugated to a metal chelating agent or chelated metal nuclide. The PSMA targeted compounds described herein can selectively recognize PSMA-expressing tumors, cancer cells, and/or cancer neovasculature in vivo and be used to deliver at least one chelated metal nuclide, such as radionuclide, to the PSMA-expressing tumors, cancer cells, and/or cancer neovasculature to treat and/or detect the PSMA-expressing tumors, cancer cells, and/or cancer neovasculature in a subject. The PSMA ligand can target and/or increase the uptake of the metal chelating agent or chelated metal nuclide in PSMA expressing cancer cells compared to untargeted metal chelated agents or chelated metal nuclides administered to a subject and decrease non-PSMA target toxicity of the metal nuclide administered (e.g., systemically) to a subject. Moreover, surprisingly it was found that the PSMA targeted compounds described herein have rapid blood clearance as well as similar standard uptake values (SUVs) in salivary glands, lacrimal glands, and non-PSMA expressing muscle tissue, and substantially lower SUVs in salivary glands, lacrimal glands, and non-PSMA expressing muscle tissue than SUVs in PSMA-expressing cancer tissue upon administration to a subject can be measured by positron emission tomography (PET).

By substantially lower SUVs in salivary glands, lacrimal glands, and non-PSMA expressing muscle tissue it is meant the PSMA targeted compounds have SUVs less than about 5%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, or less than about 95% in salivary glands, lacrimal glands, and non-PSMA expressing muscle tissue than SUVs in PSMA-expressing cancer tissue upon administration to a subject can be measured by positron emission tomography (PET).

Less non-PSMA expressing cancer tissue uptake and rapid blood clearance can allow the PSMA targeted compounds to be used in radionuclide therapy for treatment of non-castration resistant prostate cancer as primary and secondary therapeutic as well as treat other solid tumors expressing PSMA on the neovasculature and in the cancer itself, e.g., breast cancer and pancreatic cancer.

In some embodiments, the PSMA expressing cancer that is treated and/or detected is prostate cancer. In other embodiments, the cancer that is treated and/or detected can include malignant neoplasms, such a conventional (clear cell) renal carcinoma, transitional cell carcinoma of the urinary bladder, testicular embryonal carcinoma, colonic adenocarcinoma, neuroendocrine carcinoma, gliobastoma multiforme, malignant melanoma, pancreatic ductal carcinoma, non-small cell lung carcinoma, soft tissue carcinoma, breast carcinoma, and prostatic adenocarcinoma.

In some embodiments, the compound can have formula (I):

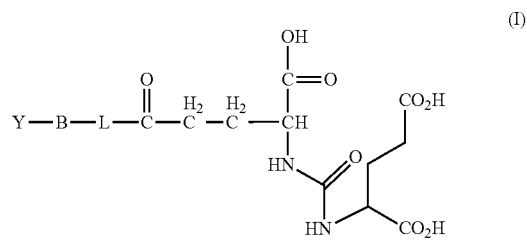

or a pharmaceutically acceptable salt thereof,
wherein:
L is a linker 3 to 11 atoms in length comprising an optionally substituted linear alkylene and a heterocyclic or cycloalkylene ring;
B is a 2 to 5 amino acid peptide linker;
Y includes at least one metal chelating agent or chelated metal nuclide.

Optional substituents for a substitutable atom in the alkylene or cycloalkylene ring described herein are those substituents that do not substantially interfere with the activity of the disclosed compounds. A "substitutable atom" is an atom that has one or more valences or charges available to form one or more corresponding covalent or ionic bonds with a substituent. For example, a carbon atom with one valence available (e.g., —C(—H)=) can form a single bond to an alkyl group (e.g., —C(-alkyl)=), a carbon atom with two valences available (e.g., —C(H$_2$)—) can form one or two single bonds to one or two substituents (e.g., —C(alkyl) (Br))—, —C(alkyl)(H)—) or a double bond to one substituent (e.g., —C=O)—), and the like. Substitutions contemplated herein include only those substitutions that form stable compounds.

For example, suitable optional substituents for substitutable carbon atoms include —F, —Cl, —Br, —I, —CN, —NO$_2$, —OR$^a$, —C(O)R$^a$, —OC(O)R$^a$, —C(O)OR$^a$, —SR$^a$, —C(S)R$^a$, —OC(S)R$^a$, —C(S)OR$^a$, —C(O)SR$^a$, —C(S)SR$^a$, —S(O)R$^a$, —SO$_2$R$^a$, —SO$_3$R$^a$, —POR$^a$R$^b$, PO$_2$R$^a$R$^b$, —PO$_3$R$^a$R$^b$, —PO$_4$R$^a$R$^b$, —P(S)R$^a$R$^b$, —P(S) OR$^a$R$^b$, —P(S)O$_2$R$^a$R$^b$, —P(S)O$_3$R$^a$R$^b$, —N(R$^a$R$^b$), —C(O)N(R$^a$R$^b$), —C(O)NR$^a$NR$^b$SO$_2$R$^c$, —C(O) NR$^a$SO$_2$R$^c$, —C(O)NR$^a$CN, —SO$_2$N(R$^a$R$^b$), —SO$_2$N (R$^a$R$^b$), —NR$^c$C(O)R$^a$, —NR$^c$C(O)OR$^a$, —NR$^c$C(O)N (R$^a$R$^b$), —C(NR$^c$)—N(R$^a$R$^b$), —NR$^d$—C(NR$^c$)—N(R$^a$R$^b$), —NR$^a$N(R$^a$R$^b$), —CRC=CR$^a$R$^b$, —C=CR$^a$, =O, =S, =CR$^a$R$^b$, =NR$^a$, =NOR$^a$, =NNR$^a$, optionally substituted alkyl, optionally substituted cycloalkyl, optionally substituted aliphatic, optionally substituted cycloaliphatic, optionally substituted heterocyclic, optionally substituted benzyl, optionally substituted aryl, and optionally substituted heteroaryl, wherein R$^a$-R$^d$ are each independently —H or an optionally substituted aliphatic, optionally substituted cycloaliphatic, optionally substituted heterocyclic, optionally substituted benzyl, optionally substituted aryl, or optionally substituted heteroaryl, or, —N(R$^a$R$^b$), taken together, is an optionally substituted heterocyclic group. Also contemplated are isomers of these groups.

Suitable substituents for nitrogen atoms having two covalent bonds to other atoms include, for example, optionally substituted alkyl, optionally substituted cycloalkyl, optionally substituted aliphatic, optionally substituted cycloaliphatic, optionally substituted heterocyclic, optionally substituted benzyl, optionally substituted aryl, optionally substituted heteroaryl, —CN, —NO$_2$, —OR$^a$, —C(O)R$^a$, —OC(O)R$^a$, —C(O)OR$^a$, —SR$^a$, —S(O)R$^a$, —SO$_2$R$^a$, —SO$_3$R$^a$, —N(R$^a$R$^b$), —C(O)N(R$^a$R$^b$), —C(O)NR$^a$NR$^b$SO$_2$R$^c$, —C(O)NR$^a$SO$_2$R$^c$, —C(O)NR$^a$CN, —SO$_2$N(R$^a$R$^b$), —SO$_2$N(R$^a$R$^b$), —NR$^c$C(O)R$^a$, —NR$^c$C(O)OR$^a$, —NR$^c$C(O)N(R$^a$R$^b$), and the like.

Suitable substituents for nitrogen atoms having three covalent bonds to other atoms include —OH, alkyl, and alkoxy (preferably C1-C4 alkyl and alkoxy). Substituted ring nitrogen atoms that have three covalent bonds to other ring atoms are positively charged, which is balanced by counteranions such as chloride, bromide, fluoride, iodide, formate, acetate and the like. Examples of other suitable counter anions are provided in the section below directed to suitable pharmacologically acceptable salts.

In some embodiments, B can consist of up to 4 amino acids selected from aspartic acid or glutamic acid and optionally one other amino acid.

In some embodiments, the compound in the absence of Y has a net negative charge under standard physiological conditions. The net negative charge of the compound can be provided by or result from the negatively charged amino acids of B, i.e., aspartic acid or glutamic acid. For example, B can include one, two, three, or four negatively charged amino acids selected from aspartic acid or glutamic acid and the optional one other amino acid of B is lysine, tyrosine, or cysteine.

In some embodiments, the negatively charged amino acid is glutamic acid and preferably D-glutamic acid. In other embodiments, the one other amino acid can be an L-amino acid.

In other embodiments, B can have the following formula:

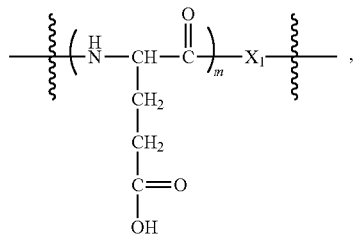

wherein m is 1, 2, 3, or 4 and $X_1$ is an amino acid, such as lysine, tyrosine, or cysteine.

A PSMA targeted compound including B as described above can have formula (II):

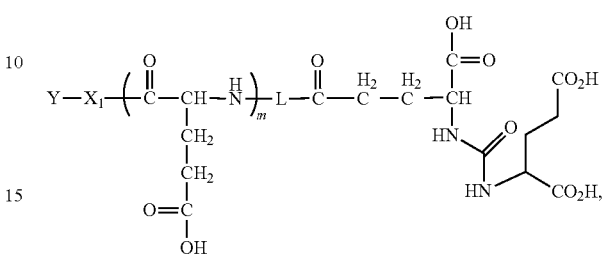

or a pharmaceutically acceptable salt thereof, wherein:
L includes a C3-C7 linear alkylene and/or a ring selected from an optionally substituted 4 to 7 membered non-aromatic heterocyclic ring or an optionally substituted C4-C7 cycloalkylene ring;
m is 1, 2, 3, or 4;
$X_1$ is an amino acid, such as lysine, tyrosine, or cysteine; and
Y includes at least one of a metal chelating agent or chelated metal nuclide.

In still other embodiments, B can have the following formula:

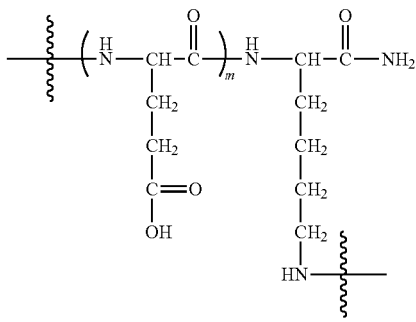

wherein m is 1, 2, 3, or 4.

A PSMA targeted compound including B as described above can have the formula (III):

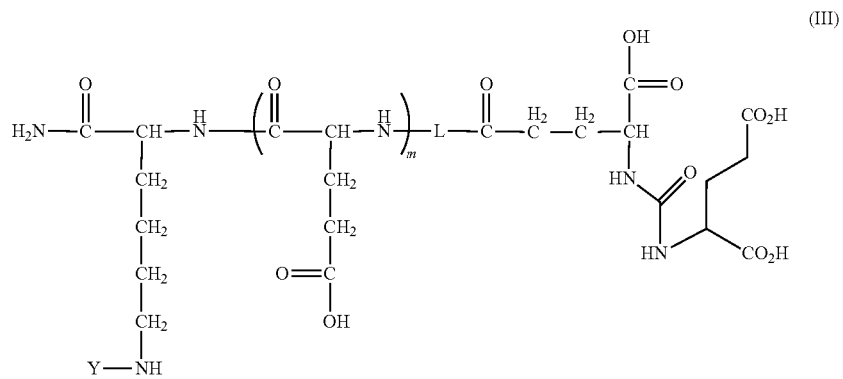

or a pharmaceutically acceptable salt thereof;

wherein
L includes a C3-C7 linear alkylene and/or a ring selected from an optionally substituted 4 to 7 membered nonaromatic heterocyclic ring or an optionally substituted C4-C7 cycloalkylene ring;
m is 1, 2, 3, or 4; and
Y includes at least one of a metal chelating agent or a chelated metal nuclide.

In some embodiments, L includes a C3-C7 linear alkylene and/or a ring selected from an optionally substituted 4 to 7 membered nonaromatic heterocyclic ring or an optionally substituted C4-C7 cycloalkylene ring.

In other embodiments, L can include at least one of an aminomethylcyclohexylic (Amc) linker and/or an aminohexanoic (Ahx) linker.

For example, a PSMA targeted compound that includes an aminomethylcyclohexylic (Amc) linker and a aminohexanoic (Ahx) linker can have the general formula:

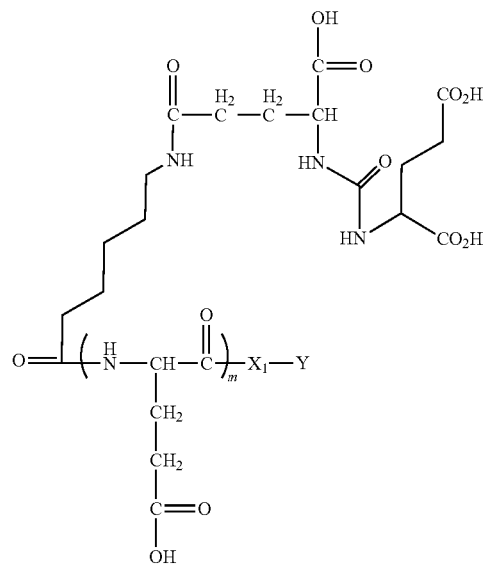

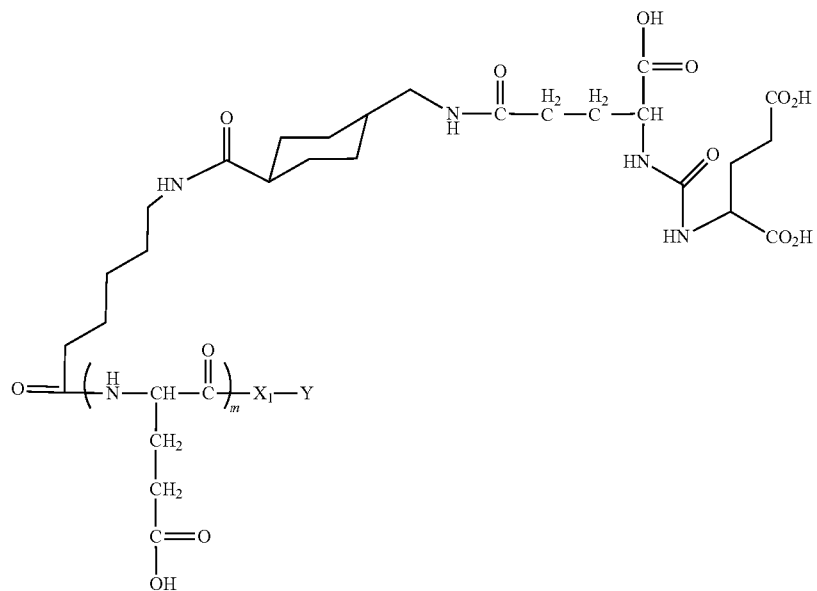

or a pharmaceutically acceptable salt thereof; wherein
m is 1, 2, 3, or 4;
$X_1$ is an amino acid, such as lysine, tyrosine or cysteine; and
Y includes at least one of a metal chelating agent or a chelated metal nuclide.

A PSMA targeted compound that includes a aminohexanoic (Ahx) linker can have the general formula:

or a pharmaceutically acceptable salt thereof; wherein
m is 1, 2, 3, or 4;
$X_1$ is an amino acid, such as lysine, tyrosine, or cysteine; and
Y includes at least one of a metal chelating agent or a chelated metal nuclide.

In particular embodiments, the compound can have the general formula:

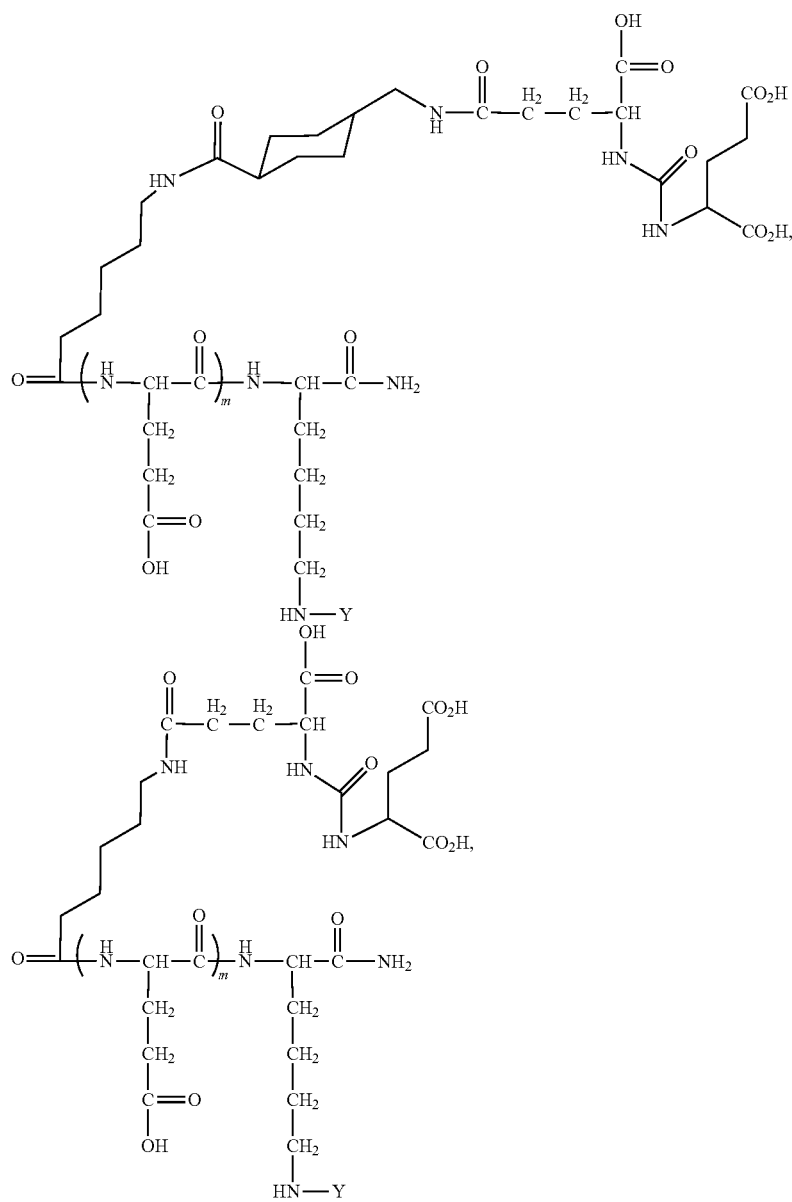

or a pharmaceutically acceptable salt thereof;
wherein,
m is 1, 2, 3, or 4; and
Y includes at least one of a metal chelating agent or a chelated metal nuclide.

In some embodiments, the metal chelating agent of Y includes at least one of diethylenetriaminepentaacetate (DTPA), 1,4,7,10-tetraazadodecanetetraacetate (DOTA), 2,2',2''-(10-(pyridin-2-ylmethyl)-1,4,7,10-tetraazacyclododecane-1,4,7-triyl) triacetic acid (DOTA-1Py), 2,2'-(7,10-(pyridin-2-ylmethyl)-1,4,7,10-tetraazacyclododecane-1,4-diyl) diacetic acid (DOTA-2Py), 2-(4,7,10-tris (pyridin-2-ylmethyl)-1,4,7,10-tetraazacyclododecane-1-yl) acetic acid (DOTA-3Py), 1,4,7,10-tetraazadodecane-1,4,7-triacetate (DO3A), ethylenediaminetetraacetate (EDTA), 1,4,7,10-tetraazacyclotridecanetetraacetic acid (TRITA), 1,4,8,11-tetraazacyclotetradecane-1,4,8,11-tetraacetic acid (TETA), 1,4,7,10-tetraazadodecanetetramethylacetate (DOTMA), 1,4,7,10-tetraazadodecane-1,4,7-trimethylacetate (DO3MA), N,N',N'',N'''-tetraphosphonatomethyl-1,4,7,10-tetraazacyclododecane (DOTP), 1,4,7,10-tetraazacyclododecane-1,4,7,10-tetrakis(methylene methylphosphonic acid) (DOTMP), 1,4,7,10-tetraazacyclododecane-1,4,7,10-tetrakis(methylene phenylphosphonic acid) (DOTPP), N,N'-ethylenedi-L-cysteine, 1,4,7-triazacyclononane (TACN), N,N'-Bis(2-hydroxy-5-(ethylene-beta-carboxy)benzyl)ethylenediamine N,N'-diacetic acid (HBED-CC), S-2-(4-isothiocyanatobenzyl)-1,4,7,10-tetraazacyclododecane tetracetic acid (p-SCN-Bn-DOTA), 2-(4-isothiocyanatobenzyl-1,4,7,10-tetraaza-1,4,7,10,tetra-(2-carbamonylmethyl)-cyclododecane (p-SCN-Bn-TCMC), MeO-DOTA-NCS, [(R)-2-Amino-3-(4-isothiocyanatophenyl)propyl]-trans-(S,S)-cyclohexane-1,2-diamine-pentaacetic acid (CHX-A''-DTPA-NCS), 2-[4-nitrobenzyl]-1,4,7,10,13-pentaazacyclopentadecane-N,N',N'',N''',N''''-pentaacetic acid (PEPA), 1,4,7,10,13,16-hexaazacyclooctadecane-N,N',N'',N''',N''''-hexaacetic acid (HEHA), desferrioxamine B (DFO), macropa, macropa-NCS, macropid, bispa², EuK-106, 7-[2-(bis-carboxymethyl-amino)-ethyl]-4,10-bis-carboxymethyl-1,4,7,10-tetraaza-cyclododec-1-yl-acetic acid (DEPA), 3p-C-DEPA, or derivatives thereof.

In other embodiments, the chelating agent is not a hexadentate chelator, such as 2,2',2"-(1,4,7-triazacyclo-nonane-1,4,7-triyl)triacetic acid (NOTA) or an analogue or derivative thereof.

In some embodiments, the metal chelating agent of Y can be directly linked to an amino acid of B with an amide bond.

In some embodiments, the chelated metal nuclide includes at least one of Ga, I, In, Y, Lu, Bi, Ac, Re, In, Th, Tc, Tl, Tb, Zr, Cu, Rb, At, Pb, Gd, Sm, or Sr.

In some embodiments, the metal chelating agent is selected or configured to chelate a therapeutic radionuclide. The therapeutic radionuclide can be selected from $^{225}$Ac, $^{226}$Ac, $^{227}$Th, $^{211}$Bi, $^{212}$Bi, $^{213}$Bi, $^{203}$Pb, $^{212}$Pb, or $^{177}$Lu.

In some embodiments, the metal nuclide can be bound to a chelating agent under mild temperature conditions, e.g., less than about 65° C., 60° C., 55° C., 50° C., 45° C., 40° C. 35° C. or 30° C. as well as elevated temperatures, e.g., greater than about 65° C., 70° C., 75° C. 80° C., 85° C., 90° C., or 95° C. In some embodiments, the mild temperature conditions are between about 10° C. and 65° C., including any value or subrange therebetween, for example, 15° C. 16° C., 17° C., 18° C., 19° C., 20° C., 21° C., 22° C., 23° C., 24° C., 25° C., 26° C., 27° C., 28° C., 29° C., 30° C., 35° C., 40° C., 45° C., 50° C., 55° C. or 60° C. In some embodiments, the metal nuclide can be conjugated to the chelating agent at room temperature, i.e., in the range of about 15° C. to about 25° C., including any temperature value therebetween.

In some embodiments, the metal nuclide can be combined with the metal chelating agent to form a metal chelate under mild pH conditions, e.g., between about 6.0 and about 8.0, including any value or subrange therebetween, e.g., 6.2, 6.4, 6.6, 6.8, 7.0, 7.2, 7.4, 7.6, or 7.8. In some embodiments the metal nuclide is a radionuclide conjugated to a chelating agent at approximately neutral pH, i.e., a pH of approximately 7.0, e.g., between about 6.8 and 7.2 including any value therebetween, e.g., 6.9, 7.0 or 7.1. In some embodiments, the radionuclide is conjugated to the chelating agent at approximately physiological pH, i.e., at approximately pH 7.4, e.g., between about 7.2 and 7.6 including any value therebetween, e.g., 7.3, 7.4 or 7.5.

In some embodiments, the radionuclide is combined with the metal chelating agent for an incubation period to allow a chelated metal complex to form. In some embodiments, the incubation period is between about 5 minutes and about 6 hours, including any period therebetween, e.g., 10, 15, 20, 25, 30, 45, 60 or 90 minutes, or 2, 3, 4 or 5 hours.

In other embodiments, the compound can have the formula of:

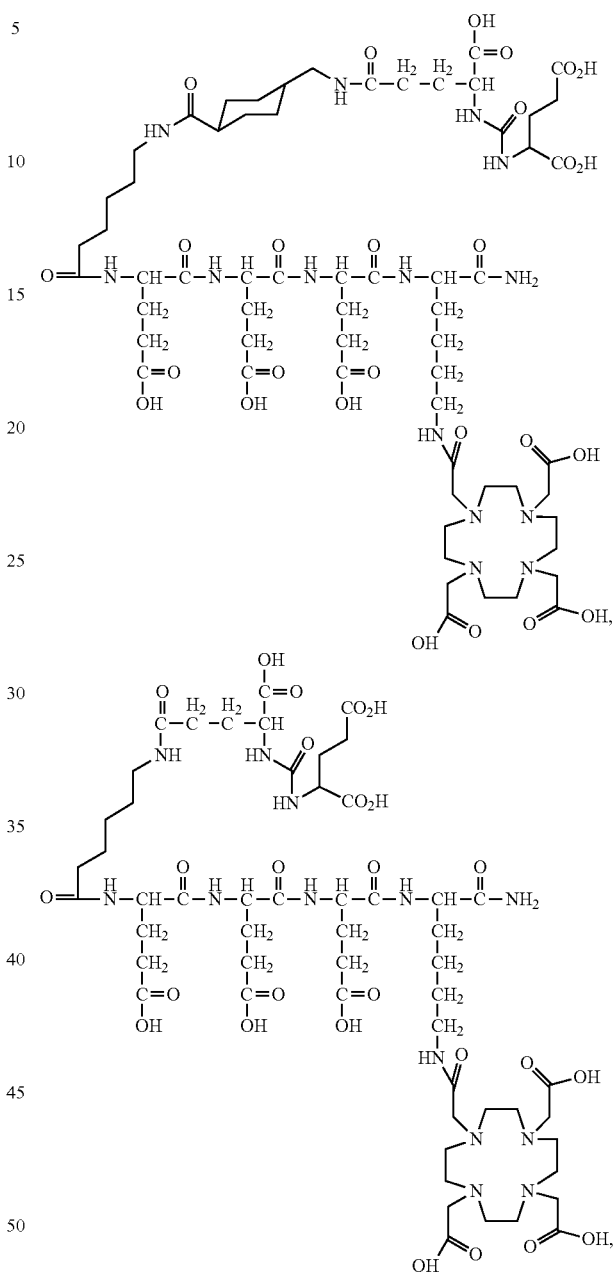

or a pharmaceutically acceptable salt thereof, optionally complexed with a metal nuclide of at least one of Ga, I, In, Y, Lu, Bi, Ac, Re, In, Th, Tc, Tl, Tb, Zr, Cu, Rb, At, Pb, Gd, Sm, or Sr. The metal nuclide can be a radionuclide selected from $^{225}$Ac, $^{226}$Ac, $^{227}$Th, $^{211}$Bi, $^{212}$Bi, $^{213}$Bi, $^{203}$Pb, $^{212}$Pb, or $^{177}$Lu.

In some embodiments, the compound has a selectivity for PSMA expressing cancer tissue versus non-PSMA expressing non-cancer tissue ≥2 times, ≥5 times, ≥10 times, ≥20 times, ≥30 times, ≥40 times, ≥50 times or more times.

In some embodiments, the PSMA targeted compounds described herein that have similar standard uptake values (SUVs) in salivary glands, lacrimal glands, and non-PSMA expressing muscle tissue, and substantially lower SUVs in salivary glands, lacrimal glands, and non-PSMA expressing muscle tissue than SUVs in PSMA-expressing cancer and/or a negative charge can also have a calculated log P (C log P) less than −10 when devoid of the chelated metal nuclide. Surprisingly and advantageously, PSMA targeted compounds having such C log P values can have an improved biodistribution and binding to PSMA expressing cancer and substantially reduced background binding to PSMA expressing non-cancer tissue, such as salivary gland tissue, compared to most existing PSMA targeting agents in the literature.

For example, PSMA-1-DOTA and JB-1498, which have similar standard uptake values (SUVs) in salivary glands, lacrimal glands, and non-PSMA expressing muscle tissue, and substantially lower SUVs in salivary glands, lacrimal glands, and non-PSMA expressing muscle tissue than SUVs in PSMA-expressing cancer, have C Log Ps of respectively −14.1786 and −13.9342 as shown below.

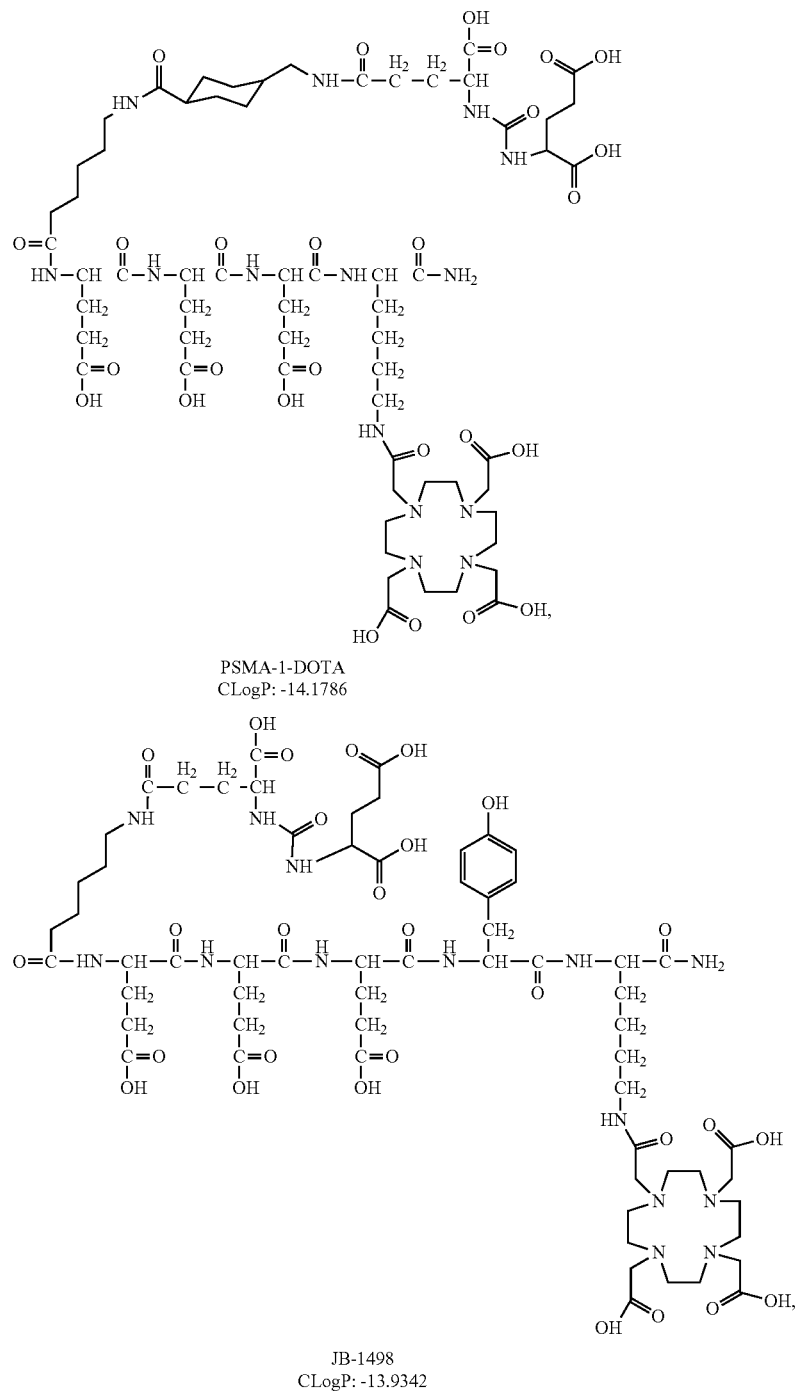

PSMA-1-DOTA
CLogP: -14.1786

JB-1498
CLogP: -13.9342

By comparison, compounds, such as PSMA-R2, PSMA-617, PSMA-11, PSMA I&T, THP-PSMA, and DCFBC, which have similar SUVs in salivary glands and PSMA-expressing cancer, have C Log Ps of respectively −4.6672, −5.9264, −3.457, −4.261, −9.62, and 1.3911 as shown below:
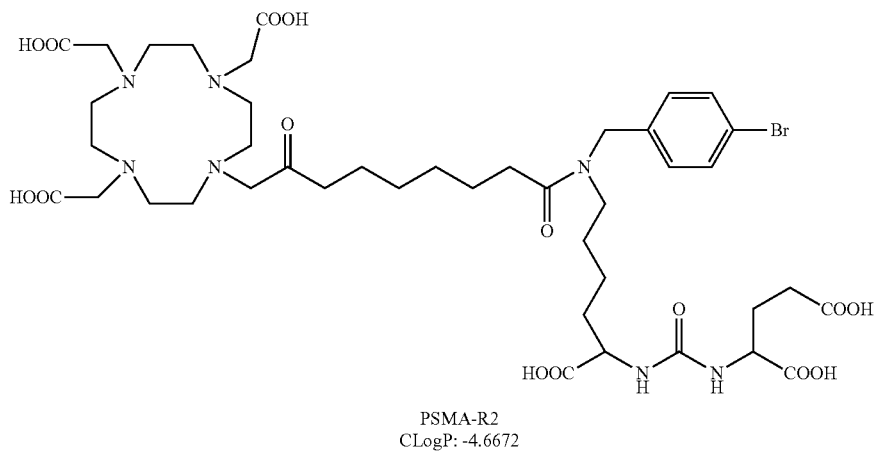
PSMA-R2
CLogP: -4.6672
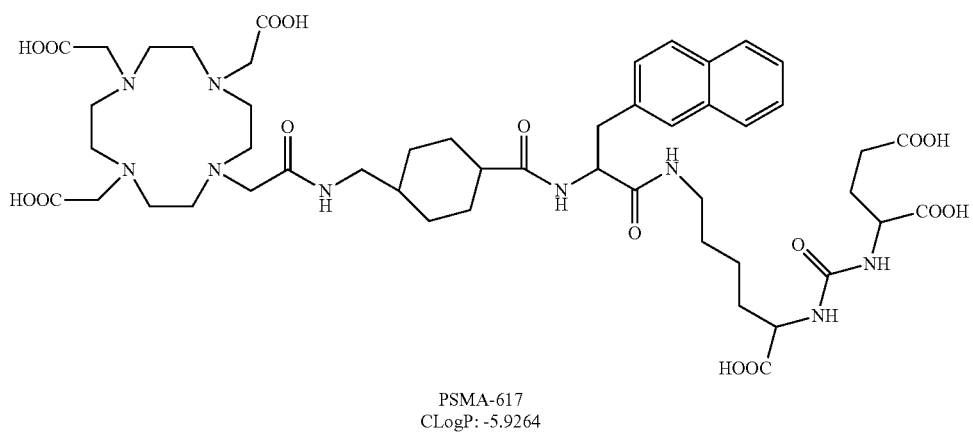
PSMA-617
CLogP: -5.9264
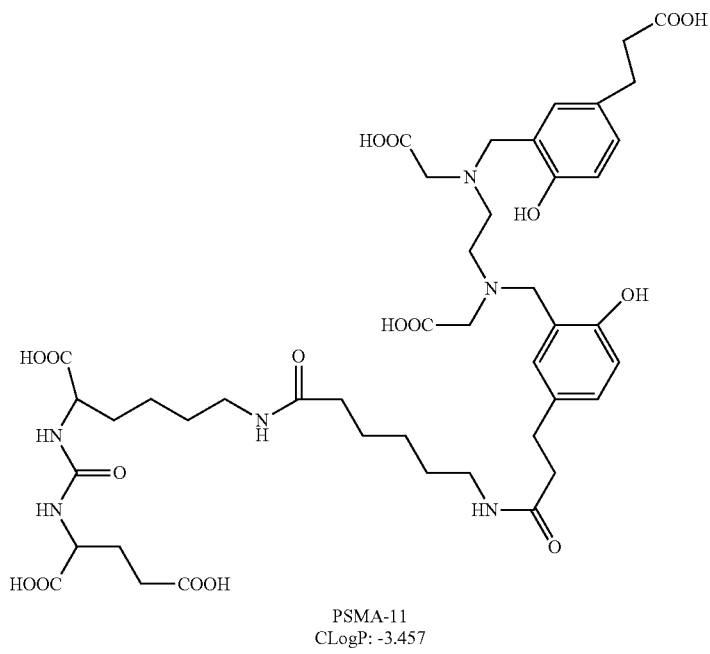
PSMA-11
CLogP: -3.457

-continued

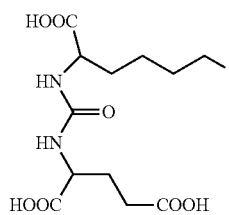
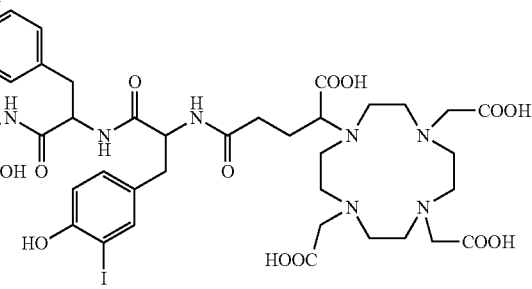

PSMA-I&T
CLogP: -4.261

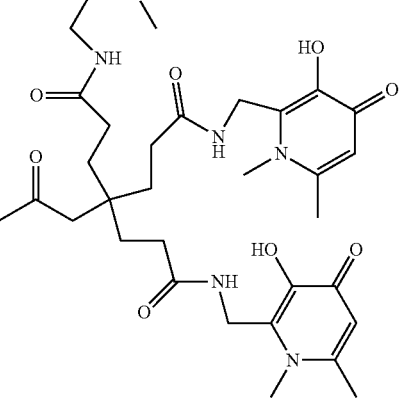

THP-PSMA
CLogP: -9.26

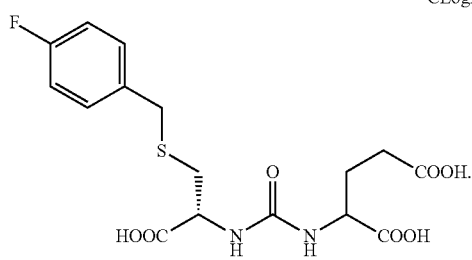

DCFBC
CLogP: 1.3911

In some embodiments, the PSMA targeted compound can be delivered to a PSMA expressing cancer tissue within the body of a mammalian subject by administering the PSMA targeted compound systemically, e.g., intravenously, to the subject. The PSMA targeted compound can be administered via a method that allows enhanced uptake or accumulation of the PSMA targeted compound at PSMA expressing cancer within the body relative to other locations in the body to selectively deliver a dose of radiation to the PSMA expressing cancer. In some embodiments, the in vivo delivered PSMA targeted compound can be used to cause cell death at the PSMA expressing cancer by delivering a targeted dose of radiation. In some embodiments, the PSMA expressing cancer cells that are killed are PSMA expressing prostate cancer cells.

In some embodiments, an in vivo radionuclide PSMA targeted compound is prepared prior to administration of the compound to a subject by combining the PSMA targeted compound with a radionuclide to form the radionuclide PSMA targeted compound. In some embodiments, the combining is carried out at a mild temperature, e.g., at a temperature where the molecule is stable. In some embodiments, the combining is carried out at a mild pH, e.g., an approximately neutral pH or an approximately physiological pH.

The PSMA targeted compounds described herein can be administered to a subject in a detectable quantity of a pharmaceutical composition containing the PSMA targeted compounds. A "detectable quantity" means that the amount of the detectable compound that is administered is sufficient to enable detection of binding of the compound to the cancer cells. An "imaging effective quantity" means that the amount of the detectable compound that is administered is sufficient to enable imaging of binding of the compound to the cancer cells.

The PSMA targeted compounds described herein can be administered to the subject by, for example, systemic, topical, and/or parenteral methods of administration. These methods include, e.g., injection, infusion, deposition, implantation, or topical administration, or any other method of administration where access to the tissue desired. In one example, administration can be by intravenous injection in the subject. Single or multiple administrations of the probe can be given. "Administered", as used herein, means provision or delivery is in an amount(s) and for a period of time(s) effective to label cancer cells in the subject.

The PSMA targeted compounds described herein administered to a subject can be used to determine the presence, location, and/or distribution of cancer cells, i.e., PSMA expressing cancer cells or PSMA expressing neovasculature of the cancer cells, in an organ or body area of a patient. The presence, location, and/or distribution of the PSMA targeted compounds in the animal's tissue, e.g., prostate cancer tissue, can be visualized (e.g., with an in vivo imaging modality described above). "Distribution" as used herein is the spatial property of being scattered about over an area or volume. In this case, "the distribution of cancer cells" is the spatial property of cancer cells being scattered about over an area or volume included in the animal's tissue, e.g., prostate tissue. The distribution of the PSMA targeted compounds may then be correlated with the presence or absence of cancer cells in the tissue. A distribution may be dispositive for the presence or absence of a cancer cells or may be combined with other factors and symptoms by one skilled in the art to positively detect the presence or absence of migrating or dispersing cancer cells, cancer metastases or define a tumor margin in the subject.

In other embodiments, the PSMA targeted compound can be used in therapeutic applications, such as to carry out targeted radionuclide therapy. For example, the PSMA targeted compound may be administered to a subject in any suitable manner, and the targeting effect imparted by PSMA ligand can be used to deliver the chelated radionuclide to a desired location within the subject's body. In some embodiments, radiation from radionuclide can be used to kill PSMA expressing cancer cells at the desired location. In some embodiments, the PSMA expressing cancer cells that are killed at the desired location are PSMA expressing prostate cancer cells. In some embodiments the PSMA targeted compound can be used to perform targeted radionuclide therapy. In some embodiments, the PSMA targeted compound can be used to perform targeted alpha therapy.

The PSMA targeted compounds can be administered alone as a monotherapy, or in conjunction with or in combination with one or more additional therapeutic agents. In some embodiments, a PSMA targeted compounds described herein can be administered to the subject in combination with an additional anti-cancer agent. In a particular embodiment, a PSMA targeted compounds as described herein can be administered to the subject in combination with anti-cancer agents, such as doxorubicin and/or docetaxel.

The term "in conjunction with" or "in combination with" indicates that the PSMA targeted compound is administered at about the same time as the additional agent. The PSMA targeted compound can be administered to the subject in need thereof as part of a pharmaceutical composition comprising the compound and a pharmaceutically acceptable carrier or excipient and, optionally, one or more additional therapeutic agents. The compound and additional therapeutic agent can be components of separate pharmaceutical compositions, which can be mixed together prior to administration or administered separately. The PSMA targeted compound can, for example, be administered in a composition containing the additional therapeutic agent, and thereby, administered contemporaneously with the agent. Alternatively, the PSMA targeted compound can be administered contemporaneously, without mixing (e.g., by delivery of the compound on the intravenous line by which the compound is also administered, or vice versa). In another embodiment, the PSMA targeted compound can be administered separately (e.g., not admixed), but within a short timeframe (e.g., within 24 hours) of administration of the compound.

The disclosed PSMA targeted compounds and additional therapeutic agents, detectable moieties, and/or theranostic agents described herein can be administered to a subject by any conventional method of drug administration. For example, parenteral administration can include, for example, intramuscular, intravenous, intraventricular, intraarterial, intrathecal, subcutaneous, or intraperitoneal administration. The disclosed compounds can also be administered orally (e.g., in capsules, suspensions, tablets or dietary), nasally (e.g., solution, suspension), transdermally, intradermally, topically (e.g., cream, ointment), inhalation (e.g., intrabronchial, intranasal, oral inhalation or intranasal drops) transmucosally or rectally. Delivery can also be by injection into the brain or body cavity of a patient or by use of a timed release or sustained release matrix delivery systems, or by onsite delivery using micelles, gels and liposomes. Nebulizing devices, powder inhalers, and aerosolized solutions may also be used to administer such preparations to the respiratory tract. Delivery can be in vivo, or ex vivo. Administration can be local or systemic as indicated. More than one route can be used concurrently, if desired. The preferred mode of administration can vary depending upon the particular disclosed compound chosen. In specific embodiments, oral, parenteral, or systemic administration (e.g., intravenous) are preferred modes of administration for treatment.

The methods described herein contemplate either single or multiple administrations, given either simultaneously or over an extended period of time. The PSMA targeted compound (or composition containing the compound) can be administered at regular intervals, depending on the nature and extent of the cancer, and on an ongoing basis. Administration at a "regular interval," as used herein, indicates that the therapeutically effective amount is administered periodically (as distinguished from a one-time dose). In one embodiment, the PSMA targeted compound is administered periodically, e.g., at a regular interval (e.g., bimonthly, monthly, biweekly, weekly, twice weekly, daily, twice a day or three times or more often a day).

The administration interval for a single individual can be fixed, or can be varied over time, depending on the needs of the individual. For example, in times of physical illness or stress, or if disease symptoms worsen, the interval between doses can be decreased. Depending upon the half-life of the agent in the subject, the agent can be administered between, for example, once a day or once a week.

For example, the administration of the PSMA targeting compound described herein and/or the additional therapeutic agent can take place at least once on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least once on week 1, 2, 3, 4, 5, 6, 7, 8, 9, 10, 11, 12, 13, 14, 15, 16, 17, 18, 19 or 20, or any combination thereof, using single or divided doses of every 60, 48, 36, 24, 12, 8, 6, 4, or 2 hours, or any combination thereof. Administration can take place at any time of day, for example, in the morning, the afternoon or evening. For instance, the administration can take place in the morning, e.g., between 6:00 a.m. and 12:00 noon; in the afternoon, e.g., after noon and before 6:00 p.m.; or in the evening, e.g., between 6:01 p.m. and midnight.

In some embodiments, the PSMA target compound may be administered to the subject at an amount effective to deliver a radiation dose, for example, at or below 1 mCi/kg (i.e., where the amount of PSMA target compound administered to the subject delivers a radiation dose of below 1000 µCi per kilogram of subject's body weight). According to certain aspects, the effective amount is at or below 900 µCi/kg, 800 µCi/kg, 700 µCi/kg, 600 µCi/kg, 500 µCi/kg, 400 µCi/kg, 300 µCi/kg, 200 µCi/kg, 150 µCi/kg, 100 µCi/kg, µCi/kg, 60 µCi/kg, 50 µCi/kg, 40 µCi/kg, 30 µCi/kg, 20 µCi/kg, 10 µCi/kg, 5 µCi/kg, or 1 µCi/kg. According to certain aspects, the effective amount of the radiation dose from the PSMA targeted compound is at least 1 µCi/kg, 2.5 µCi/kg, 5 µCi/kg, 10 µCi/kg, 20 µCi/kg, 30 µCi/kg, 40 µCi/kg, 50 µCi/kg, 60 µCi/kg, 70 µCi/kg, 80 µCi/kg, 90 µCi/kg, 100 µCi/kg, 150 µCi/kg, 200 µCi/kg, 250 µCi/kg, 300 µCi/kg, 350 µCi/kg, 400 µCi/kg or 450 µCi/kg. According to certain aspects, the PSMA targeted compound may be administered at an amount effective to deliver a radiation dose that includes any combination of upper and lower limits as described herein, such as from at least 5 mCi/kg to at or below 50 µCi/kg, or from at least 50 mCi/kg to at or below 500 µCi/kg.

In other embodiments, the PSMA targeted compound may be administered to the subject at an amount effective to deliver a radiation dose and the effective amount of radiation dose delivered may be at or below 2 mCi (i.e., wherein the PSMA targeted compound is administered to the subject in a non-weight-based dosage). According to certain aspects, the effective dose of the radiation delivered by the PSMA targeted compound may be at or below 1 mCi, such as 0.9 mCi, 0.8 mCi, 0.7 mCi, 0.6 mCi, 0.5 mCi, 0.4 mCi, 0.3 mCi, 0.2 mCi, 0.1 mCi, 90 µCi, 80 µCi, 70 µCi, 60 µCi, 50 µCi, 40 µCi, 30 µCi, 20 µCi, 10 µCi, or 5 µCi. The effective amount of PSMA targeted compound may be at least 2 µCi, such as at least 5 Ci, 10 µCi, 20 µCi, 30 µCi, 40 µCi, 50 µCi, 60 µCi, 70 µCi, 80 µCi, 90 µCi, 100 µCi, 200 µCi, 300 µCi, 400 µCi, 500 µCi, 600 µCi, 700 µCi, 800 µCi, 900 µCi, 1 mCi, 1.1 mCi, 1.2 mCi, 1.3 mCi, 1.4 mCi, or 1.5 mCi. According to certain aspects, the PSMA targeted compound may be administered at an amount effective to deliver a radiation dose that includes any combination of upper and lower limits as described herein, such as from at least 2 µCi to at or below 1 mCi, or from at least 2 µCi to at or below 250 µCi, or from 75 µCi to at or below 400 µCi.

In other embodiments, the PSMA targeted compound can be administered in a single dose that delivers less than 12 Gy, or less than 8 Gy, or less than 6 Gy, or less than 4 Gy, or less than 2 Gy, such as doses of 2 Gy to 8 Gy, to the subject, such as predominantly to the targeted PSMA expressing cancer.

In still other embodiments, the PSMA targeting compound may be provided in a total amount of up to or equal to 100 mg, such as up to or equal to 60 mg, such as 5 mg to 45 mg, or a total amount of from 0.001 mg/kg patient weight to 3.0 mg/kg patient weight, such as from 0.005 mg/kg patient weight to 2.0 mg/kg patient weight, or from 0.01 mg/kg patient weight to 1 mg/kg patient weight, or from 0.1 mg/kg patient weight to 0.6 mg/kg patient weight, or 0.3 mg/kg patient weight, or 0.4 mg/kg patient weight, or 0.5 mg/kg patient weight, or 0.6 mg/kg patient weight.

The amount of administered PSMA targeted compound and/or additional therapeutic agent administered to the subject can depend on the characteristics of the subject, such as general health, age, sex, body weight and tolerance to drugs as well as the degree, severity and type of rejection. The skilled artisan will be able to determine appropriate dosages depending on these and other factors using standard clinical techniques.

In addition, in vitro or in vivo assays can be employed to identify desired dosage ranges. The dose to be employed can also depend on the route of administration, the seriousness of the disease, and the subject's circumstances. Effective doses may be extrapolated from dose-response curves derived from in vitro or animal model test systems. The amount of the compound can also depend on the disease state or condition being treated along with the clinical factors and the route of administration of the compound.

The disclosed PSMA targeted compound and/or additional therapeutic agent described herein can be administered to the subject in conjunction with an acceptable pharmaceutical carrier or diluent as part of a pharmaceutical composition for therapy. Formulation of the PSMA targeted compound to be administered will vary according to the route of administration selected (e.g., solution, emulsion, capsule, and the like). Suitable pharmaceutically acceptable carriers may contain inert ingredients that do not unduly inhibit the biological activity of the PSMA targeted compounds. The pharmaceutically acceptable carriers should be biocompatible, e.g., non-toxic, non-inflammatory, non-immunogenic and devoid of other undesired reactions upon the administration to a subject. Standard pharmaceutical formulation techniques can be employed, such as those described in Remington's Pharmaceutical Sciences, ibid. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

The preparation of a pharmacological composition that contains active ingredients dissolved or dispersed therein is well understood in the art. Typically, such compositions are prepared as injectables as either liquid solutions or suspensions, however, solid forms suitable for solution, or suspensions, in liquid prior to use can also be prepared. Formulation will vary according to the route of administration selected (e.g., solution, emulsion, capsule).

A pharmaceutically acceptable carrier for a pharmaceutical composition can also include delivery systems known to the art for entraining or encapsulating drugs, such as anticancer drugs. In some embodiments, the disclosed compounds can be employed with such delivery systems including, for example, liposomes, nanoparticles, nanospheres, nanodiscs, dendrimers, and the like. See, for example Farokhzad, O. C., Jon, S., Khademhosseini, A., Tran, T. N., Lavan, D. A., and Langer, R. (2004). "Nanoparticle-aptamer bioconjugates: a new approach for targeting prostate cancer cells." Cancer Res., 64, 7668-72; Dass, C. R. (2002). "Vehicles for oligonucleotide delivery to tumours." J.

Pharm. Pharmacol., 54, 3-27; Lysik, M. A., and Wu-Pong, S. (2003). "Innovations in oligonucleotide drug delivery." J. Pharm. Sci., 92, 1559-73; Shoji, Y., and Nakashima, H. (2004). "Current status of delivery systems to improve target efficacy of oligonucleotides." Curr. Pharm. Des., 10, 785-96; Allen, T. M., and Cullis, P. R. (2004). "Drug delivery systems: entering the mainstream." Science, 303, 1818-22. The entire teachings of each reference cited in this paragraph are incorporated herein by reference.

The following examples are for the purpose of illustration only and are not intended to limit the scope of the claims, which are appended hereto.

EXAMPLE

PSMA is expressed by most solid tumors and tumor neovasculature. We expected that PSMA would be a suitable biomarker for positron emission tomography (PET) molecular imaging. We synthesized a PSMA-targeted PET contrast agent with [$^{68}$Ga]PSMA-1-DOTA.

Synthesis of Glu-CO-Glu'-Amc-Ahx-dGlu-dGlu-dGlu-Lys-NH$_2$ (PSMA-1)

PSMA-1 was synthesized manually using standard Fmoc chemistry. Generally, peptide was synthesized at 0.2 mmol scale starting from C-terminal Fmoc-rink amide MBHA resin. Fmoc-deprotection at each cycle was carried out using 20% pipperidine in DMF. Coupling reactions were carried out using 3.3 equiv of Fmoc-amino acids in DMF activated with 3.3 equiv of HCTU and 5 equiv of diisopropylethylamine (DIPEA) in DMF. These steps were repeated each time with an amino acid added. After the peptide sequence Fmoc-Glu'-Amc-Ahx-dGlu-dGlu-dGlu-Lys(Mtt) was built on the resin, the Fmoc group of N-terminal amino acid Glu' was deprotected by 20% pipperidine. Then, a chloroform solution containing 3 eq of H-Glu(OtBu)-OtBu mixed with 2.5 eq of DIPEA were prepared. The solution is then added slowly to equal molar of triphosgene in chloroform over 10 minutes at room temperature. After 15 minute incubation to allow for isocyanate formation, the reaction mixture was mixed with Glu'-Amc-Ahx-dGlu-dGlu-dGlu-Lys(Mtt) on rink amide resin pre-swollen in chloroform with 2.5 eq of DIPEA. After the reaction was complete, the resin was washed with DMF and then dichloromethane and dried. The peptide was cleaved from resin by TFA/water/triisopropylsilane (950:25:25). The cleaved peptide was purified by preparative HPLC.

Synthesis of PSMA-1-DOTA

Method 1

PSMA-1 (5 mg, 4.6 μmol) was dissolved in 1 mL PBS, then 3 equivalent of DOTA NHS ester was added to the solution. The pH of the reaction mixture was adjust to 7.5 to 8.0. The mixture was stirred at room temperature overnight, and was purified by HPLC.

Method 2

Alternatively, PSMA-1-DOTA can be synthesized on solid phase. The Mtt group on Glu-CO-Glu'-Amc-Ahx-dGlu-dGlu-dGlu-Lys(Mtt)-rink amide resin (synthesized above) can be removed by 2% TFA. The resin will be washed with 2% DIPEA in DMF and resuspend in DMF, then 3 equivalent of DOTA NHS ester and 3 equivalent of DIPEA will be added. When the reaction is completed as indicated by ninhydrin test, the peptide will be cleaved from the resin and purified by HPLC.

Synthesis of [68Ga]PSMA-1-DOTA

The synthesis of [$^{68}$Ga]GaPSMA-1-DOTA (FIG. 1) was carried out based on a protocol described by Scintomics GmbH for routine production of [$^{68}$Ga]GaPSMA-11. This protocol was improved and validated at UH PET radiopharmacy, and generator elution mode was set up in accordance with Eckert & Ziegler directives for IGG-100 generator elution. This resulted into elimination of unwanted side-products formation and the total radiosynthesis yield is improved. The entire synthesis, including elution of radioactive gallium from the generator with 0.1 M hydrochloric acid, conjugation with PSMA-1 peptide, purification and formulation of the final product are automated by Scintomics GRP® synthesizer and controlled by the software using GMP-manufactured single-use sterile cassettes. All reagent vials, syringes, filters and cartridges are provided by ABX Advanced Chemical Compounds, GmbH unless otherwise stated. Reagents are purchased separately and are of the highest grade.

Post synthesis, the sterile filter type Cathivex GV is removed and placed in the vessel for filter integrity test.

The samples for QC, sterility and control probe are manually dispensed and measured for activity in the dose calibrator.

The typical decay corrected chemical yield is 65±10%. The drug substance is not isolated. Instead, the drug substance is collected directly through a 0.22 μm sterilizing filter into a vented sterile vial Samples are removed for analysis of product quality.

Figure 2:
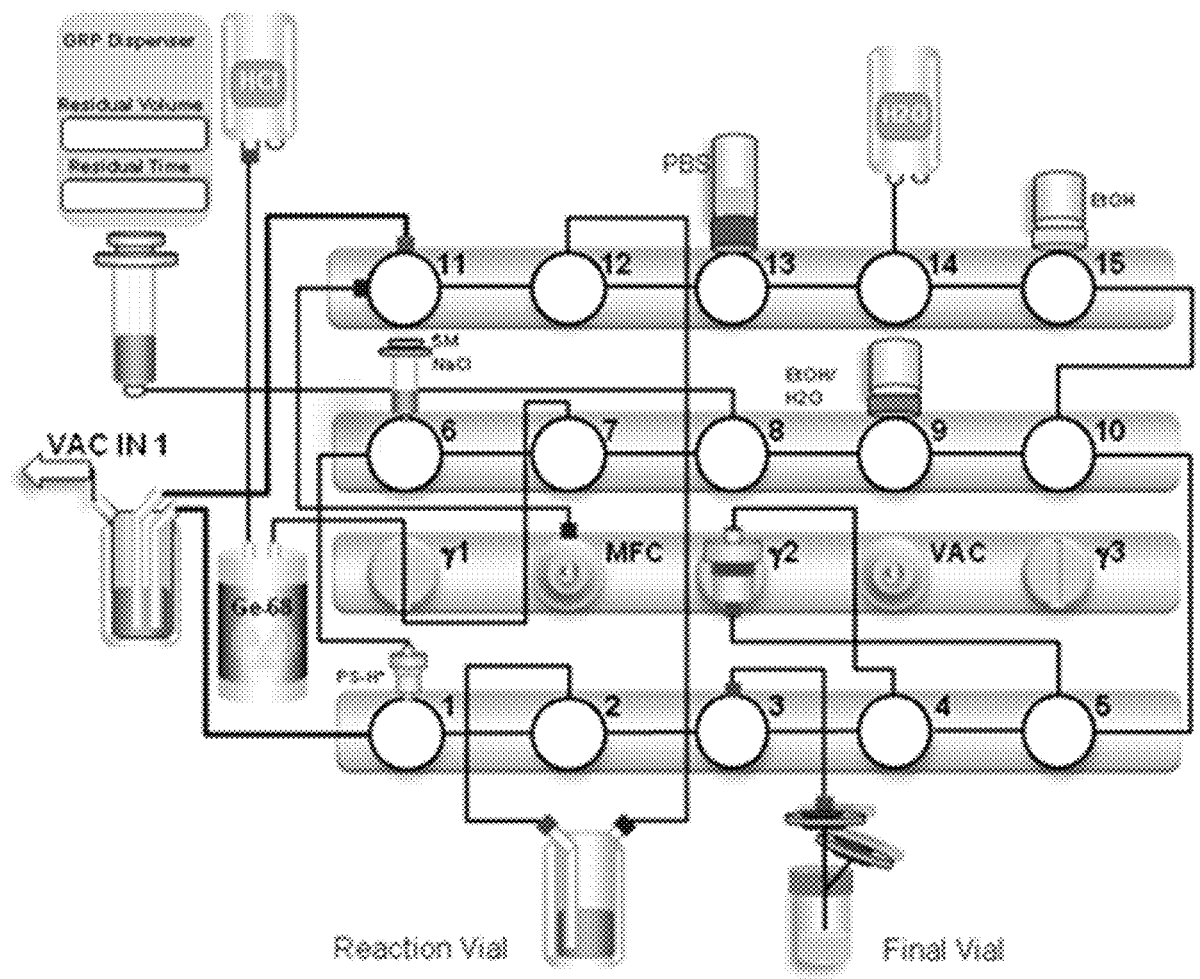
FIG. 2 illustrates the installation of cassette and reagents for the synthesis of [$^{68}$Ga]PSMA-1 using Scintomics GRP® automated synthesizer.

Referring to FIG. 2, the automated synthesizer for the manufacturing of [$^{68}$Ga]PSMA-1-DOTA is an automated synthesis module Scintomics GRP® manufactured by Scintomics GmbH (Germany) for clinical GMP production of PET probes. The module consists of four valve units, reactor unit and control unit. The commercially available GMP kit for this synthesizer is manufactured by ABX (Germany) and includes the disposable cassette, set of disposable supplies (syringes, needles, filters) and the set of necessary reagents. The cassette consists of 3 manifolds with 3-way valves, which are operated by valve units. The movement of reagents and solutions inside the cassette is provided either by mechanical (syringe pump) or gas force (vacuum pump, nitrogen flow). The cassette is mounted and reagents are installed in accordance with manufacturer's guidelines. Once cassette and reagents are installed, the synthesizer becomes fully-closed system, and the whole module is operated by Scintomics® GRP Software via PC, mounted outside the mini-cell. This synthesis module allows for minimizing the radioactive exposure of personnel and assures the level of radioactivity in production lab at the background level. The final product is delivered automatically into product vial inside the ISOS unit in the dispensing box for QC sampling.

Competition Binding Assay

We first conjugated a macrocyclic DOTA to our PSMA-1 ligand enabling us to label it with [$^{68}$Ga]. We then compared the macrocyclic-conjugated PSMA-1 ligand to PSMA-11 ligand, PSMA I&T ligand, and ZJ24 ligand in a competitive radio-binding assay using [$^3$H]-ZJ24 with PC3pip cells.

FIG. 3 illustrates that the PSMA-1 ligand conjugated to DOTA, the PSMA-1 ligand has approximately 4-5 fold higher affinity for PSMA.

Stability Assay

Figure 4:
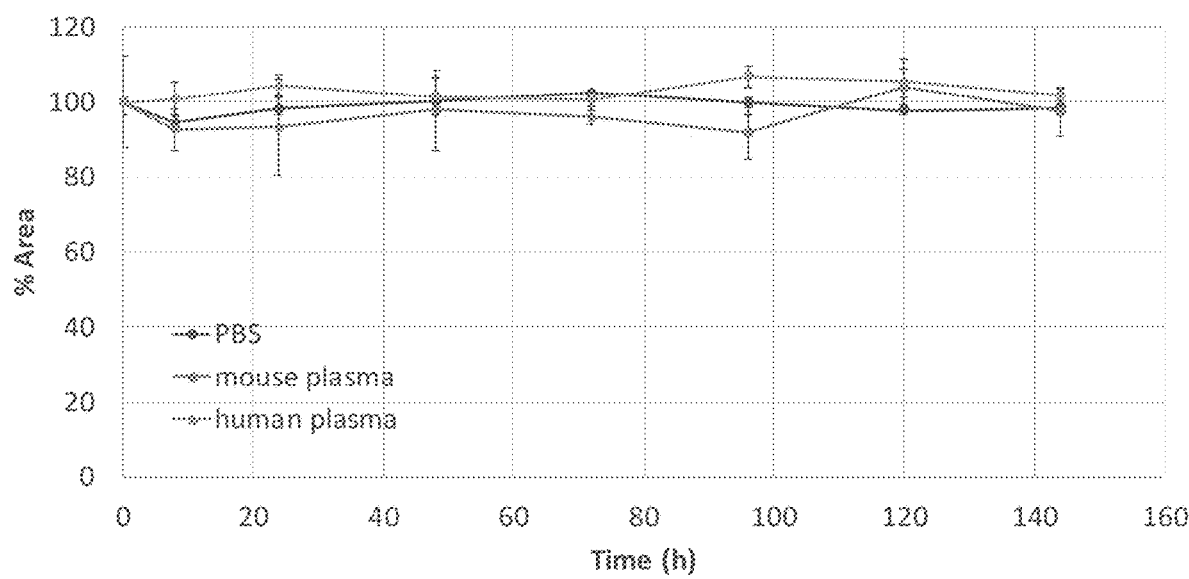
FIG. 4 illustrates a graph comparing PSMA-1-DOTA stability in PBS, mouse plasma, and human plasma over time.

PSMA-1-DOTA was incubated in 100% mouse Plasma, PBS, or 100% human plasma at 37° C. As illustrated in FIG. 4, at the indicated times a portion of the incubated PSMA-1-DOTA was analyzed by HPLC to track degradation/purity. No decline in the product was noted for 7 days suggesting stability of the PSMA-1-DOTA in both mouse serum and PBS. Other studies have shown stability for long term storage as a lyophilized powder. And stability has been monitored and confirmed for at least 7 days frozen in isotonic sterile saline.

In Vivo Imaging

We compared the [$^{68}$Ga]-PSMA-11 and the [$^{68}$Ga]-PSMA-1-DOTA ligand in healthy animals without tumor. Equal doses of radioactivity were injected into the same animal (a single animal was used to limit variability). We injected the [$^{68}$Ga]-PSMA-1-DOTA first to prevent blockade of its binding by the other ligand, waited 24 hours and then injected the other radiolabeled ligand. As is evident if FIG. 5, while the [$^{68}$Ga]-PSMA-11 had significant uptake in the salivary glands, none was noted for the [$^{68}$Ga]-PSMA-1-DOTA. Further PSMA-1-DOTA had faster renal clearance and less renal retention of the probe. (all images are approximately the same dose, and displayed at the same scale).

Figure 7:
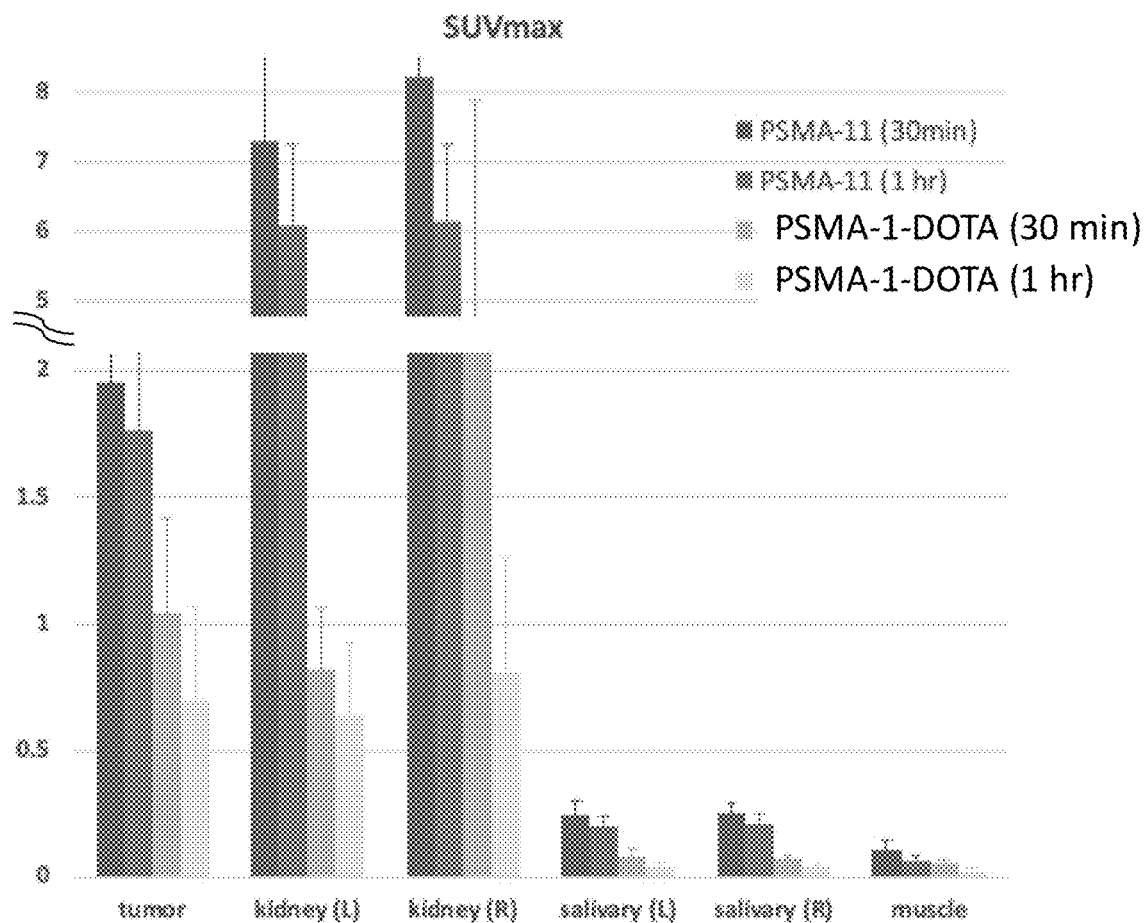
FIG. 7 illustrates a graph comparing standard uptake values of [$^{68}$Ga]PSMA-1-DOTA and [$^{68}$Ga]PSMA-11 in various tissues of tumor bearing mice.

We also made a similar comparison using animals harboring PC3pip tumors that overexpress PSMA. FIGS. 6 and 7 indicate that [$^{68}$Ga]-PSMA-1-DOTA showed no uptake into salivary glands, less kidney uptake, but similar (but less) uptake in the PC3pip tumor. In contrast, [$^{68}$Ga]-PSMA-11 showed significant uptake into the salivary and lacrimal glands and also into the kidneys as well as the tumor. (all images are approximately the same dose, and displayed at the same scale). When comparing FIG. 2 (no tumor) with the animals bearing tumor there is no sinking effect, where the tumor uptake can prevent the salivary uptake.

Figure 8:
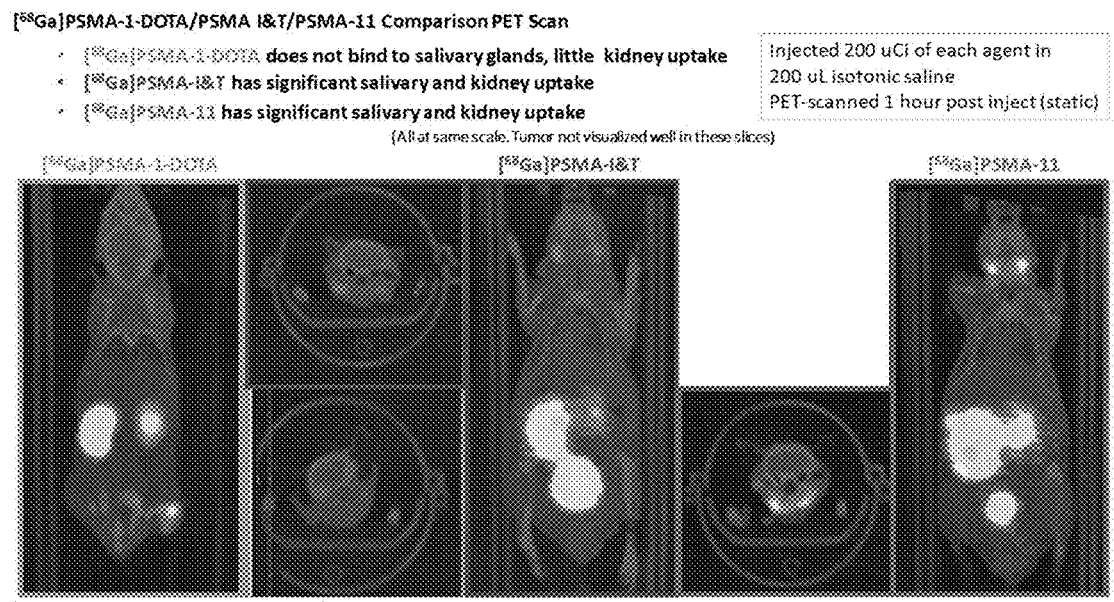
FIG. 8 illustrates images of PET scans of tumor bearing mice administered [$^{68}$Ga]PSMA-1-DOTA, [$^{68}$Ga]PSMA I&T, or [$^{68}$Ga]PSMA-11.
Figure 9:
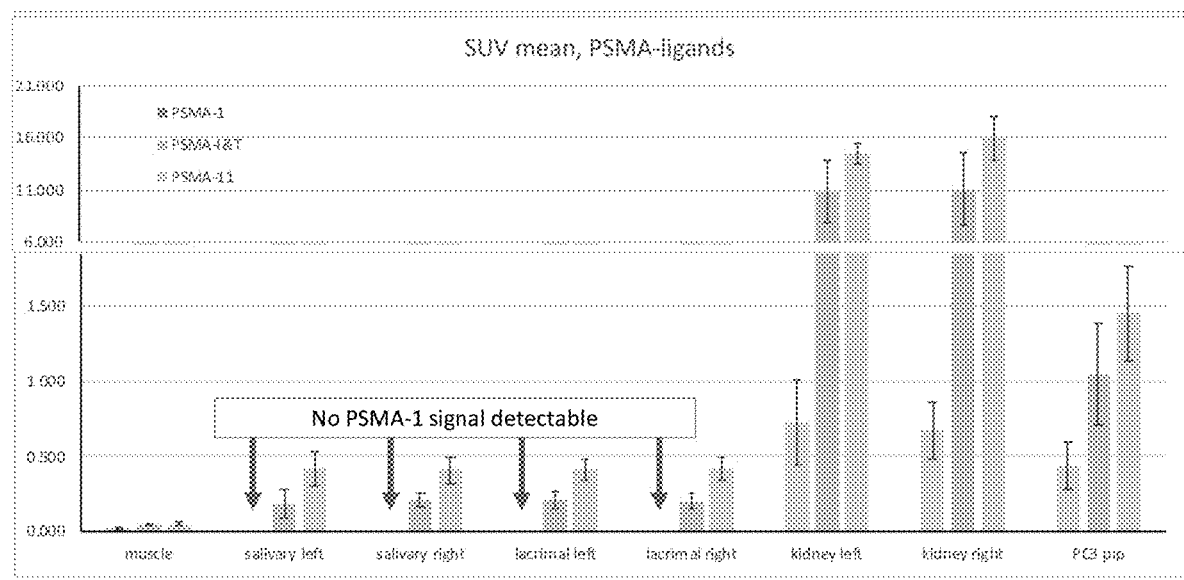
FIG. 9 illustrates a graph showing standard uptake values of [$^{68}$Ga]PSMA-1-DOTA, [$^{68}$Ga]PSMA I&T, or [$^{68}$Ga]PSMA-11 in various tissues of tumor bearing mice.

FIGS. 8 and 9 illustrate the results of PET scans performed 1 hour after 200 μCi $^{68}$Ga labeled probe using same animal. PSMA-1-DOTA was injected first, then after 24 hours PSMA-I&T was injected and scanned, then 3 days later PSMA-11 was injected and scanned. Probes were all labeled with Ga from a newly replenished gallium generator. At least three animals were used for each determination of SUV.

Figure 10:
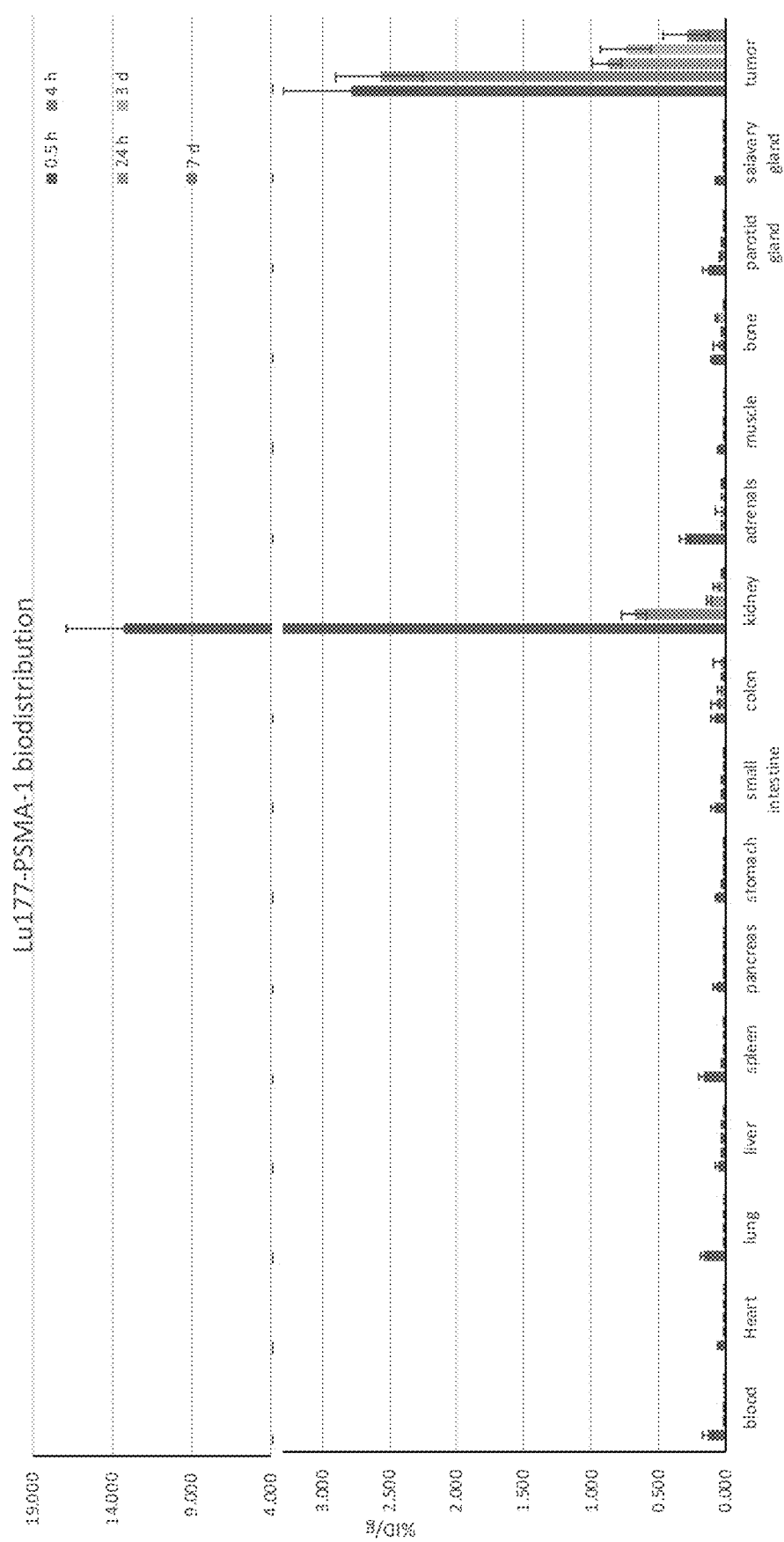
FIG. 10 illustrates a graph showing biodistribution of [$^{177}$Lu]PSMA-1-DOTA administered to tumor bearing mice at various time points.
Figure 11:
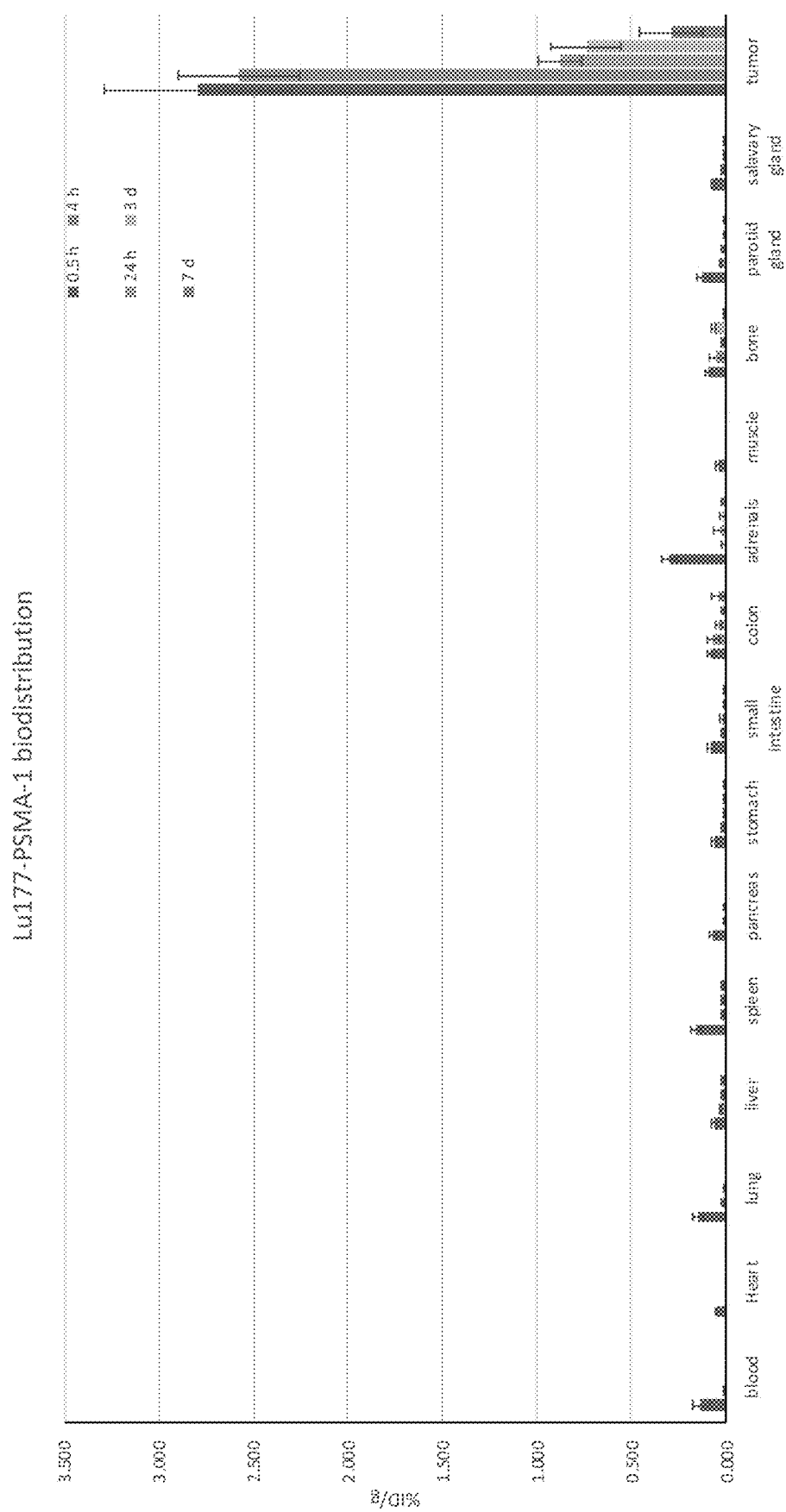
FIG. 11 illustrates the graph of FIG. 10 without the kidney data.

FIGS. 10 and 11 illustrate graphs showing biodistribution of [$^{177}$Lu]PSMA-1-DOTA administered to tumor bearing mice at various time points with and without the kidney data. In each case 3 animals were utilized for the BioD assessment for each time point. Animals received 75 μCi of PSMA-1-DOTA in 100 μl isotonic saline. pAnimals were sacrificed at the indicated times after probe injection, dissected and the tissue sampled weighed and counted.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A compound having the formula of:

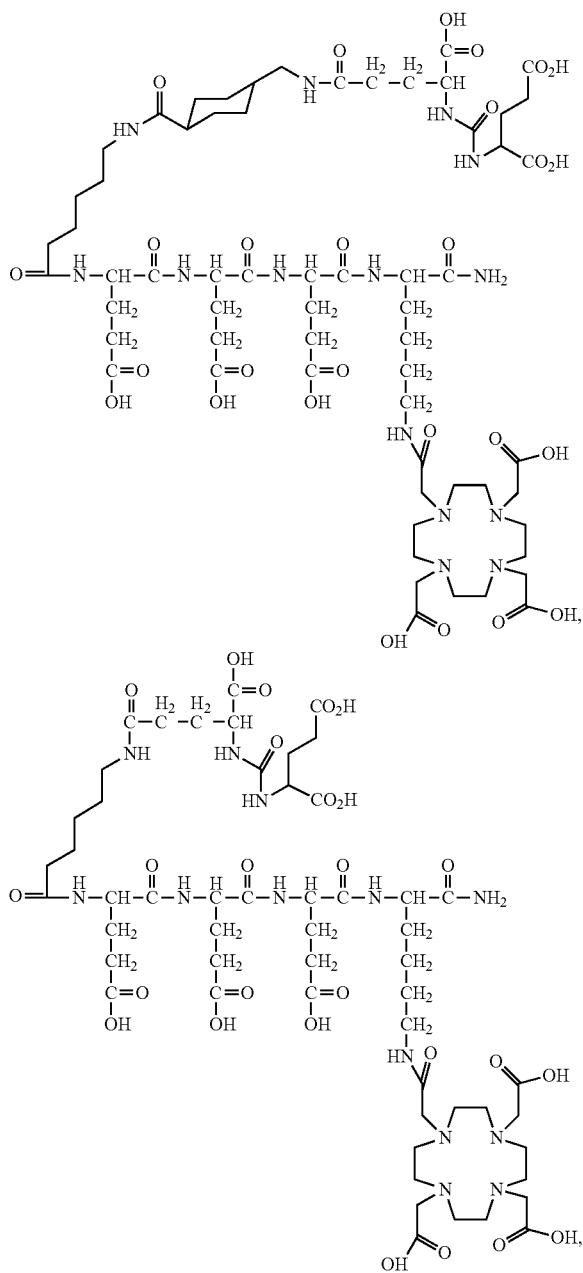

or a pharmaceutically acceptable salt thereof, chelated to a radionuclide selected from $^{225}$Ac, $^{226}$Ac, $^{227}$Th, $^{211}$Bi, $^{212}$Bi, $^{213}$Bi, $^{203}$Pb, $^{212}$Pb, or $^{177}$Lu.

* * * * *